US010582945B2

(12) United States Patent
Boudreaux

(10) Patent No.: US 10,582,945 B2
(45) Date of Patent: Mar. 10, 2020

(54) SURGICAL DEVICES AND SYSTEMS WITH ROTATING END EFFECTOR ASSEMBLIES HAVING AN ULTRASONIC BLADE

(71) Applicant: Ethicon LLC, Guaynabo, PR (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 162 days.

(21) Appl. No.: 15/926,751

(22) Filed: Mar. 20, 2018

(65) Prior Publication Data

US 2019/0290318 A1  Sep. 26, 2019

(51) Int. Cl.
| | | |
|---|---|---|
| A61B 17/32 | (2006.01) | |
| A61B 34/35 | (2016.01) | |
| A61B 34/30 | (2016.01) | |
| A61B 17/00 | (2006.01) | |
| A61B 17/29 | (2006.01) | |
| A61B 18/00 | (2006.01) | |

(52) U.S. Cl.
CPC ...... *A61B 17/320092* (2013.01); *A61B 34/30* (2016.02); *A61B 34/35* (2016.02); *A61B 2017/00305* (2013.01); *A61B 2017/00327* (2013.01); *A61B 2017/00331* (2013.01); *A61B 2017/00367* (2013.01); *A61B 2017/00398* (2013.01); *A61B 2017/00734* (2013.01); *A61B 2017/2929* (2013.01); *A61B 2017/320074* (2017.08); *A61B 2017/320094* (2017.08); *A61B 2018/0063* (2013.01); *A61B 2018/00589* (2013.01); *A61B 2018/00601* (2013.01); *A61B 2034/302* (2016.02)

(58) Field of Classification Search
CPC ....... A61B 2017/320094; A61B 2017/320074; A61B 2017/00367; A61B 2017/00398; A61B 17/320092; A61B 17/320068; A61B 34/35
See application file for complete search history.

(56) References Cited

U.S. PATENT DOCUMENTS

| | | | |
|---|---|---|---|
| 5,792,135 | A | 8/1998 | Madhani et al. |
| 5,893,835 | A | 4/1999 | Witt et al. |
| 5,944,737 | A | 8/1999 | Tsonton et al. |
| 6,056,735 | A | 5/2000 | Okada et al. |
| 6,132,368 | A | 10/2000 | Cooper |
| 6,231,565 | B1 | 5/2001 | Tovey et al. |

(Continued)

FOREIGN PATENT DOCUMENTS

| | | |
|---|---|---|
| EP | 1698289 A2 | 9/2006 |
| EP | 3082626 A1 | 10/2016 |

(Continued)

OTHER PUBLICATIONS

International Search Report and Written Opinion for PCT/US2018/042295 dated Oct. 25, 2018 (15 pages).

(Continued)

*Primary Examiner* — Wade Miles
*Assistant Examiner* — Mikail A Mannan
(74) *Attorney, Agent, or Firm* — Mintz Levin Cohn Ferris Glovsky and Popeo, P.C.

(57) ABSTRACT

Surgical devices and systems having rotating end effector assemblies for treating tissue are provided. Methods for using the same are also provided.

19 Claims, 10 Drawing Sheets

(56) References Cited

U.S. PATENT DOCUMENTS

| | | |
|---|---|---|
| 6,364,888 B1 | 4/2002 | Niemeyer et al. |
| 6,669,690 B1 | 12/2003 | Okada et al. |
| 6,783,524 B2 | 8/2004 | Anderson et al. |
| 7,520,865 B2 | 4/2009 | Radley Young et al. |
| 7,524,320 B2 | 4/2009 | Tierney et al. |
| 7,621,930 B2 | 11/2009 | Houser |
| 7,691,098 B2 | 4/2010 | Wallace et al. |
| 7,780,659 B2 | 8/2010 | Okada et al. |
| 7,806,891 B2 | 10/2010 | Nowlin et al. |
| 7,824,401 B2 | 11/2010 | Manzo et al. |
| 8,574,228 B2 | 11/2013 | Okada et al. |
| 8,672,935 B2 | 3/2014 | Okada et al. |
| 8,986,302 B2 | 3/2015 | Aldridge et al. |
| 9,095,367 B2 | 8/2015 | Olson et al. |
| 9,351,753 B2 | 5/2016 | Balanev et al. |
| 9,351,754 B2 | 5/2016 | Vakharia et al. |
| 9,408,622 B2 | 8/2016 | Stulen et al. |
| 9,445,816 B2 | 9/2016 | Swayze et al. |
| 9,585,658 B2 | 3/2017 | Shelton, IV |
| 2006/0058825 A1 | 3/2006 | Ogura et al. |
| 2012/0292367 A1 | 11/2012 | Morgan et al. |
| 2015/0209059 A1 | 7/2015 | Trees et al. |
| 2015/0320437 A1 | 11/2015 | Worrell et al. |
| 2016/0296250 A1 | 10/2016 | Olson et al. |
| 2016/0296251 A1 | 10/2016 | Olson et al. |
| 2016/0296252 A1 | 10/2016 | Olson et al. |
| 2016/0296268 A1 | 10/2016 | Gee et al. |
| 2016/0302819 A1 | 10/2016 | Stulen et al. |
| 2016/0374712 A1 | 12/2016 | Stulen et al. |
| 2017/0095295 A1 | 4/2017 | Overmyer |
| 2017/0196637 A1* | 7/2017 | Shelton, IV ..... A61B 17/07207 |
| 2017/0202571 A1 | 7/2017 | Shelton, IV et al. |
| 2017/0202599 A1 | 7/2017 | Shelton, IV et al. |
| 2017/0202609 A1* | 7/2017 | Shelton, IV ....... A61B 18/1445 |
| 2018/0000543 A1 | 1/2018 | Hibner |
| 2018/0049813 A1 | 2/2018 | Yates et al. |
| 2019/0021752 A1 | 1/2019 | Boudreaux |
| 2019/0021756 A1 | 1/2019 | Boudreaux |

FOREIGN PATENT DOCUMENTS

| | | |
|---|---|---|
| WO | 2003082133 A1 | 10/2003 |
| WO | 2014148898 A1 | 9/2014 |
| WO | 2014151621 A1 | 9/2014 |
| WO | 2014151952 A1 | 9/2014 |
| WO | 2016168184 A1 | 10/2016 |

OTHER PUBLICATIONS

U.S. Appl. No. 16/012,287, filed Jun. 19, 2018, Surgical Devices and Systems With Rotating End Effector Assemblies Having an Ultrasonic Blade.

U.S. Appl. No. 15/994,755, filed May 31, 2018, Ultrasonic Transducer to Blade Acoustic Coupling, Connections, and Configurations.

U.S. Appl. No. 15/654,428, filed Jul. 19, 2017, Ultrasonic Transducer to Blade Acoustic Coupling, Connections, and Configurations.

* cited by examiner

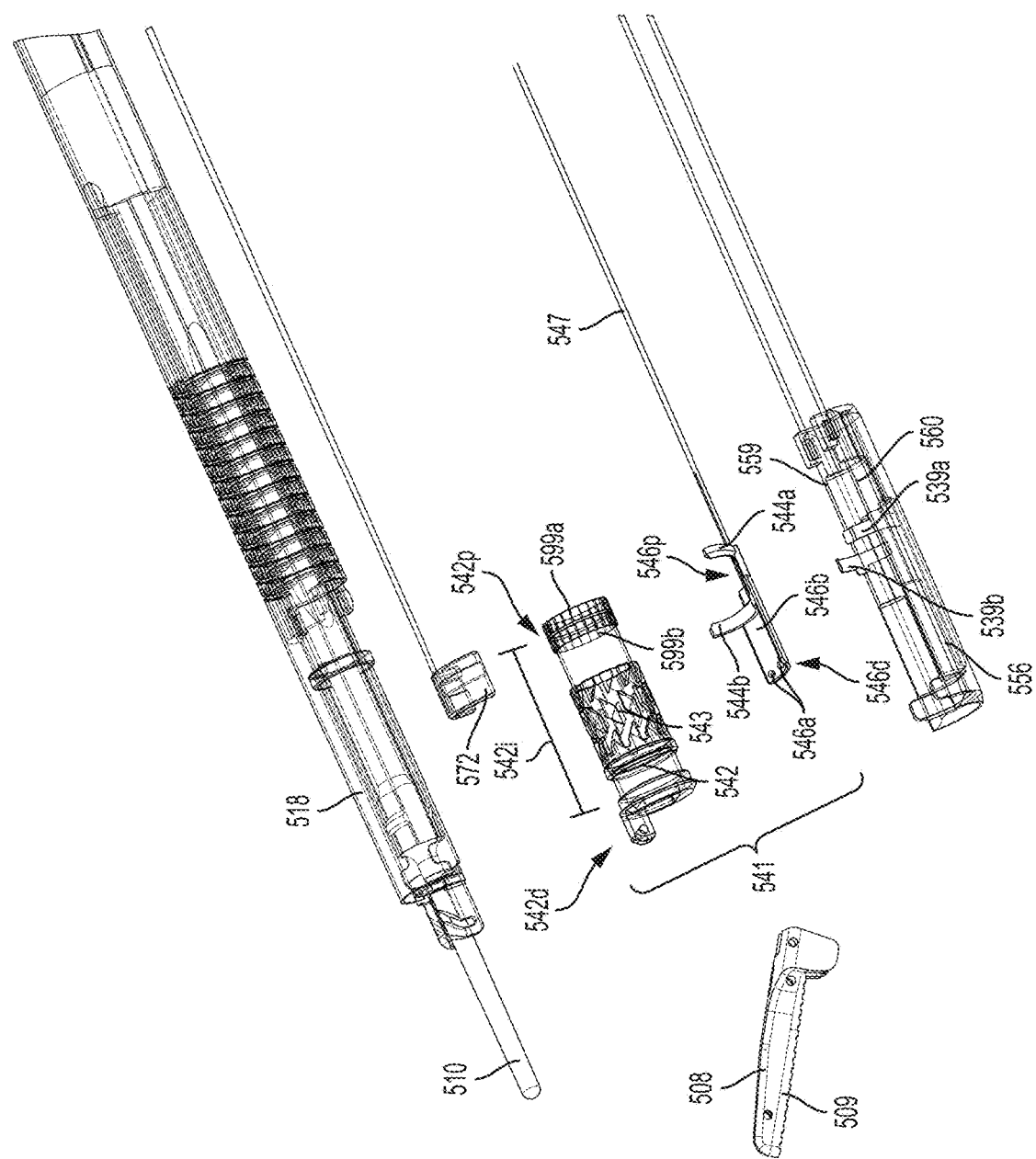

SURGICAL DEVICES AND SYSTEMS WITH ROTATING END EFFECTOR ASSEMBLIES HAVING AN ULTRASONIC BLADE

FIELD

Surgical devices and systems with rotating end effector assemblies and methods for using the same are provided for treating tissue.

BACKGROUND

A variety of surgical devices include an end effector assembly having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Movement of the end effector assembly during use of these surgical devices can be important for sufficient access to tissue. In robotic surgery, movement of the end effector assembly can also facilitate coordinated movement of the surgeon's hands and the end effector assembly. Any lack of movement can lead to various opportunities for user errors, for example, inadequate cutting or sealing of tissue and accidental damage to the anatomy during surgery. As such, it can be desirable to have the end effector assembly move with six degrees of motion (e.g., surge, heave, sway, yaw, pitch, and roll).

Accordingly, despite existing technologies, there remains a need for improved surgical devices and systems and methods for treating tissue.

SUMMARY

Surgical devices and systems and methods for using the same are provided.

In one exemplary embodiment, a surgical device is provided and can include a housing having an ultrasonic transducer positioned therein, an instrument shaft extending from the housing, and an end effector assembly having a clamping element and an ultrasonic blade. The instrument shaft can include an outer sleeve having an articulable region and a non-articulable region, a waveguide, and a rotation assembly having an inner sleeve that can be coupled to the clamping element. The end effector assembly can be at a distal end of the outer sleeve. The waveguide can be acoustically coupled with the ultrasonic transducer, where a portion of the articulable region can be aligned with a flexible portion of the waveguide. The ultrasonic blade can be in acoustic communication with the waveguide. The inner sleeve can have a sliding mechanism that can be configured to selectively rotate the clamping element relative to the ultrasonic blade. In one aspect, the housing can be attached to a robotic surgical system.

The sliding mechanism can have a variety of configurations. For example, in one aspect, the sliding mechanism can include a substantially spiral slot and a pin housed within the substantially spiral slot such that the pin can be configured to selectively slide within the substantially spiral slot upon a force applied to an input operatively coupled to the pin to thereby cause rotation of the inner sleeve relative to the instrument shaft. In another aspect, the sliding mechanism can include a predetermined pattern of projections that project radially outward from the inner sleeve to form channels therebetween, and one or more pins that can be configured to selectively slide within the channels upon a force applied to an input operatively coupled to the one or more pins to thereby cause rotation of the inner sleeve relative to the outer sleeve.

In some aspects, the instrument shaft can include two spring arms that can each be configured to engage a plurality of teeth that extend circumferentially around a proximal end of the inner sleeve. The first spring arm can be configured to engage a first plurality of teeth to prevent rotation of the inner sleeve relative to the outer sleeve in a first direction. The second spring arm can be configured to engage a second plurality of teeth to prevent rotation of the inner sleeve relative to the outer sleeve in a second direction.

In other aspects, the instrument shaft can include a clamping assembly coupled to the end effector assembly. The clamping assembly can be configured to drive movement of the clamping element relative to the instrument shaft such that the clamping element selectively moves towards and away from the ultrasonic blade. The clamping assembly can include a clamp pull that can be coupled to the clamping element, where the clamp pull can be configured to axially translate relative to the outer sleeve to cause the clamping element to move towards and away from the ultrasonic blade.

In one aspect, the device can also include an articulation assembly that can be configured to selectively deflect the end effector assembly from a position aligned with a longitudinal axis, where the longitudinal axis extends along the non-articulable region of the outer sleeve.

In another exemplary embodiment, a robotic surgical system is provided and can include an electromechanical arm having a motor disposed therein, an instrument housing mounted to the electromechanical arm, where the instrument housing can have an ultrasonic transducer disposed therein, an instrument shaft extending from the housing, and an end effector assembly having a jaw and an ultrasonic blade. The instrument shaft can include an outer sleeve having the end effector assembly formed at a distal end thereof. The instrument shaft can also include an articulable ultrasonic waveguide acoustically coupled to the ultrasonic transducer and extending through the instrument shaft, and an actuation assembly having a first actuator rod that can be operably coupled to the motor. The ultrasonic blade can be acoustically coupled to the articulable ultrasonic waveguide. The actuation assembly can be operatively coupled to the jaw. The first actuator rod can be configured to axially translate relative to the instrument shaft to selectively rotate the jaw while the ultrasonic blade remains stationary.

In one aspect, the actuation assembly can include a second actuator rod that can be operable coupled to the motor. The second actuator rod can be configured to axially translate relative to the outer sleeve to selectively move the jaw towards and away from the ultrasonic blade.

In some aspects, the instrument shaft can include a rotation assembly. The rotation assembly can have variety of configurations. For example, in one aspect, the rotation assembly can include an inner sleeve having a substantially spiral slot that at least partially extends along a length of the inner sleeve, and a pin housed within the slot and coupled to a distal end of the first actuator rod. The pin can be configured to selectively slide from a first position to a second position within the slot upon axial translation of the first actuator rod to thereby rotate the inner sleeve relative to the instrument shaft. In another aspect, the rotation assembly can include an inner sleeve that includes a predetermined pattern of projections that project radially outward from the inner sleeve to form channels therebetween and one or more pins coupled to a distal end of the first actuator rod. The one or more pins can be configured to selectively slide within the channels upon axial translation of the first actuator rod to cause rotation of the inner sleeve relative to the instrument shaft.

In some aspects, the instrument shaft can include a locking mechanism that can be configured to selectively promote unidirectional rotation of the jaw. In other aspects, the instrument shaft can include a clamping assembly having a jaw pull that can be configured to axially translate relative to the outer sleeve to thereby cause the jaw to open and close so as to clamp tissue between the jaw and the ultrasonic blade.

In one aspect, the system can also include an articulation assembly that can be configured to deflect the end effector assembly from a position aligned with a longitudinal axis, where the longitudinal axis extends along a non-articulable section of the outer sleeve.

Methods for using surgical devices and systems are also provided. In one embodiment, the method can include directing a surgical device having an end effector assembly to a surgical site. The end effector assembly can be operably coupled to an instrument shaft that contains an ultrasonic waveguide. The method can also include selectively rotating the clamping element relative to the ultrasonic blade, selectively actuating a clamping assembly to cause the clamping element to move towards the ultrasonic blade to and thereby apply a clamping force to tissue disposed between the clamping element and the ultrasonic blade, and transmitting ultrasonic energy to the ultrasonic blade to treat the tissue clamped between the clamping element and the ultrasonic blade.

In some aspects, the method can also include selectively articulating the instrument shaft such that the end effector assembly can be angularly oriented with respect to a longitudinal axis of a proximal portion of the instrument shaft extending from a housing. In such aspects, the clamping element can rotate when the clamping element is in an articulated condition.

In one aspect, the clamping element can rotate in the range of about 1 degree to about 360 degrees. In another aspect, the instrument shaft can be attached to a robotic surgical system.

BRIEF DESCRIPTION OF THE DRAWINGS

This invention will be more fully understood from the following detailed description taken in conjunction with the accompanying drawings, in which:

FIG. 5B is a partially exploded view of the distal portion of the surgical device of FIG. 5A;

DETAILED DESCRIPTION

Figure 1:
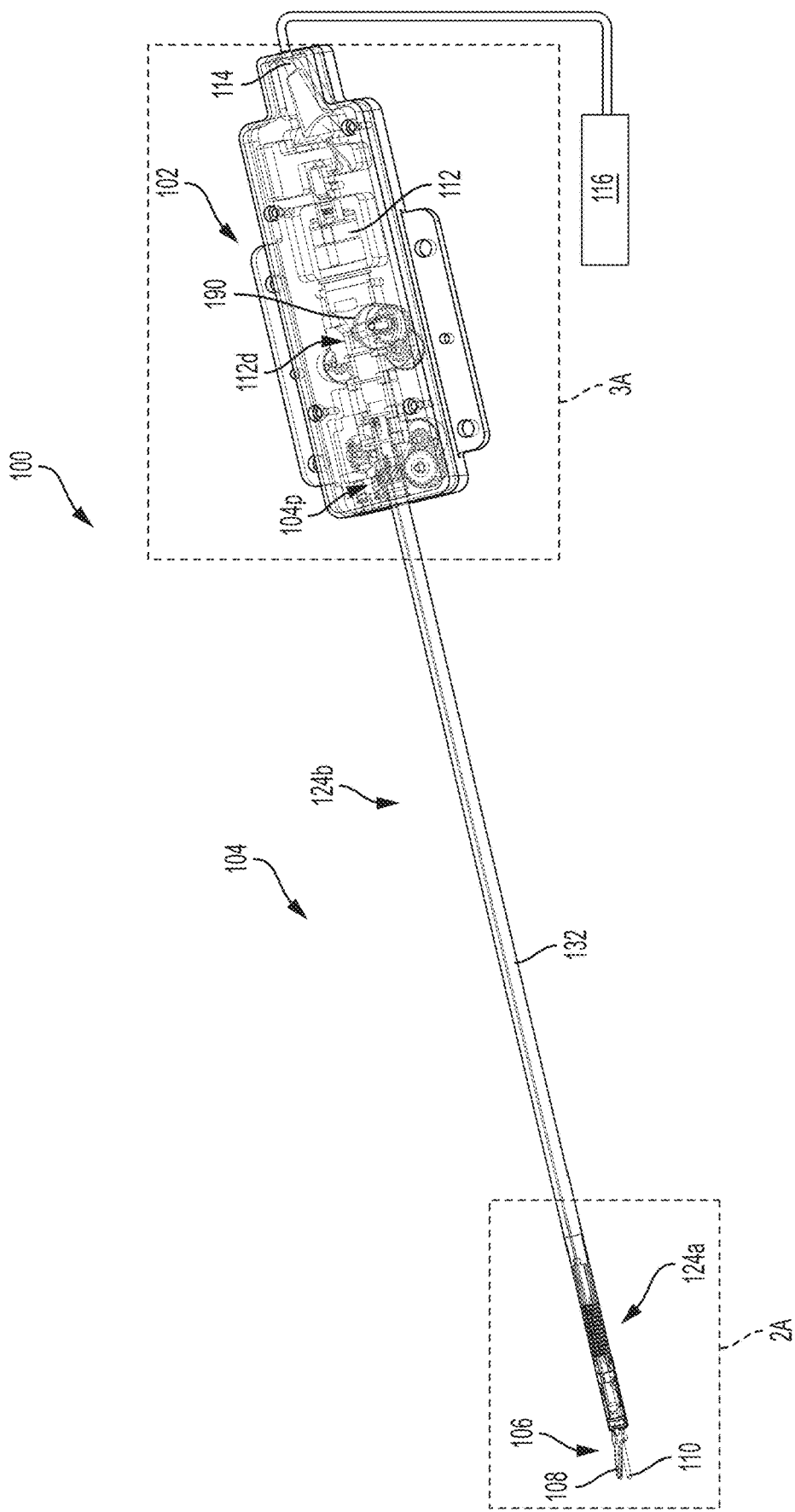
FIG. 1 is a perspective, partially transparent view of an exemplary embodiment of a surgical device having a rotation assembly having an inner sleeve.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of a device or to a user, such as a robot, having a housing mounted thereto. Other spatial terms such as "front" and "rear" similarly correspond respectively to distal and proximal. It will be further appreciated that for convenience and clarity, spatial terms such as "vertical" and "horizontal" are used herein with respect to the drawings. However, components of surgical device are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Surgical devices that utilize ultrasonic energy to treat (e.g., cut or seal) tissue provide a particularly useful surgical option. In some surgical situations it can be useful or necessary to move the end effector assembly, which includes an ultrasonic blade and clamping arm or element, in different orientations to access a surgical site. While an end effector assembly with an ultrasonic blade and clamping arm or element can rotate in its entirety, articulation of the end effector assembly can be more limited. For example, the ultrasonic blade can be acoustically coupled to a waveguide having a thinned section in an area where the blade is to bend as the end effector assembly is articulated. However, the articulation is limited to only one plane and thus a full range of motion of the end effector assembly cannot be achieved. That is, the clamping arm or element of the end effector assembly is aligned with the articulation plane, and thus cannot be rotated out of plane. A solution to this problem is disclosed herein in which, in addition to articulation, the end effector assembly can be manipulated such that the clamp arm or element is able to be rotated independent of the ultrasonic blade, and thus the waveguide. The result of this feature is to effectively enable the rotation of the clamping arm or element out of plane of the articulation plane, thereby facilitating six degrees of freedom of the end effector assembly when it is in an articulated condition.

Surgical devices and systems methods of using the same are provided. In general, a surgical device is provided having at least a housing and an instrument shaft extending therefrom. As discussed in greater detail below, the surgical device can be configured such that a portion of an end effector assembly can rotate while the remaining portion thereof remains stationary. In certain exemplary aspects, the instrument shaft can include an outer sleeve having an end effector assembly at a distal end thereof. The end effector assembly can include a clamping element and an ultrasonic blade in which the clamping element is configured to selectively rotate relative to the ultrasonic blade via a rotation assembly coupled to the clamping element. The instrument shaft can also include additional assemblies, for example, an articulation assembly that is configured to selectively deflect the end effector assembly and/or a clamping assembly that is configured to selectively move the clamping element towards and away from the ultrasonic blade. Thus, unlike conventional surgical devices, the surgical devices provided herein can be configured to impart the end effector assembly with six degrees of motion. For example, in contrast to conventional surgical devices, the clamping element can rotate while the ultrasonic blade remains stationary when the end effector assembly is in articulated conditions.

An exemplary surgical device can include a variety of features to facilitate partial or complete movement of the end effector assembly, as described herein and illustrated in the drawings. However, a person skilled in the art will appreciate that the surgical devices can include only some of these features and/or it can include a variety of other features known in the art. The surgical devices described herein are merely intended to represent certain exemplary embodiments. Further, a person skilled in the art will appreciate that the surgical devices described herein have application in conventional minimally-invasive and open surgical instrumentation as well as application in robotic-assisted surgery. That is, the surgical devices described herein can be disposed within a handle assembly designed for a hand-held device or designed to be mounted to an electromechanical arm (e.g., a robotic arm).

As discussed in more detail below, exemplary embodiments of surgical devices are provided that are configured to facilitate various movements of the end effector assembly, including rotational movement of the entire end effector assembly, selective rotation of the clamping element relative to the ultrasonic blade, as well as articulation of the end effector assembly. The instrument shaft includes a rotation assembly having a sliding mechanism that is configured to selectively rotate the clamping element about the ultrasonic blade while the ultrasonic blade remains stationary. Further, the instrument shaft can include additional assemblies, such as an articulation assembly that can facilitate articulation of the end effector assembly. As such, the surgical devices described herein can be configured to rotate and articulate the end effector assembly.

Figure 6:
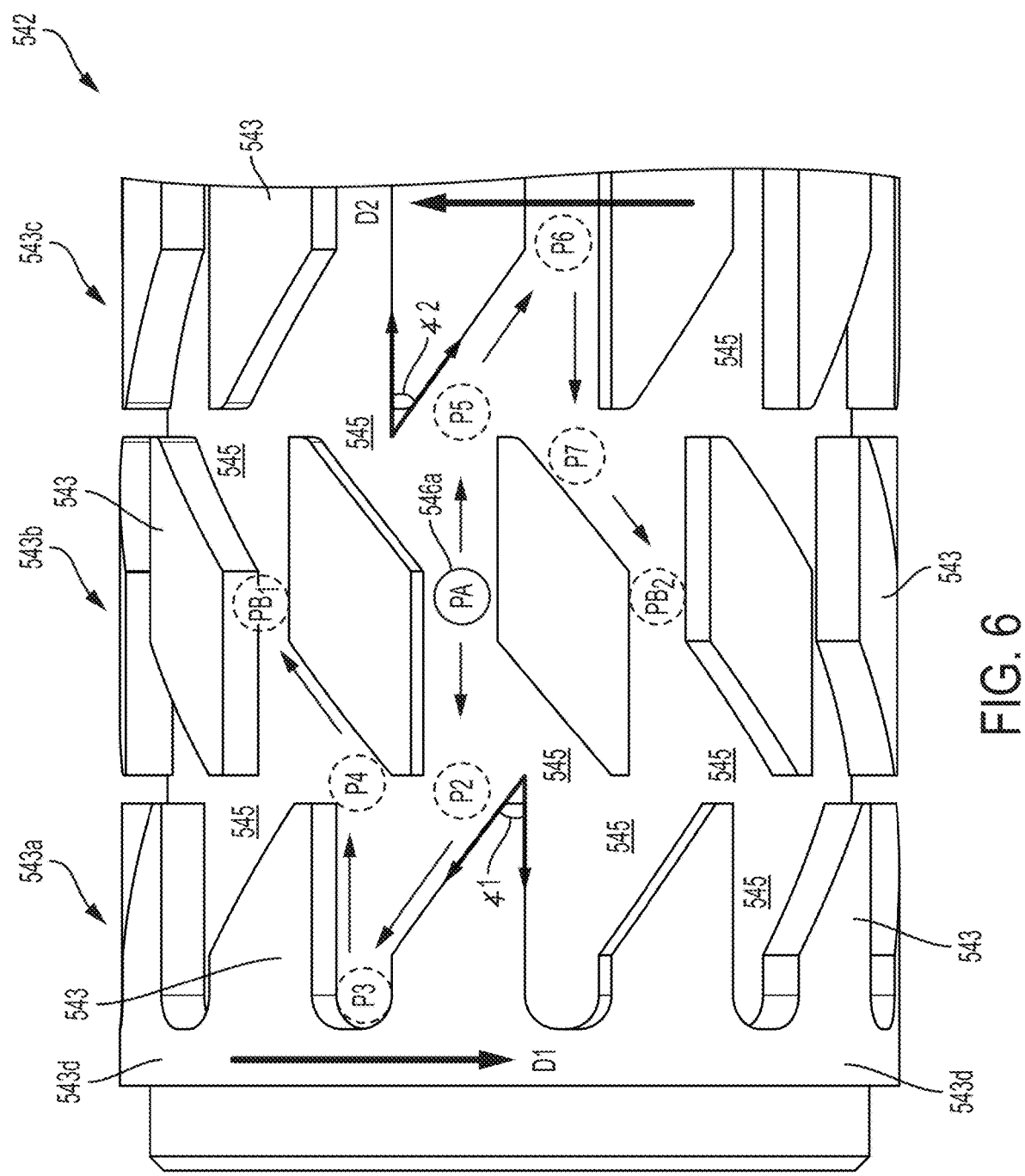
FIG. 6 is a magnified view of a portion of the inner sleeve of the rotation assembly of FIG. 5A, showing exemplary movement of a pin through channels defined within the inner sleeve.
Figure 7:
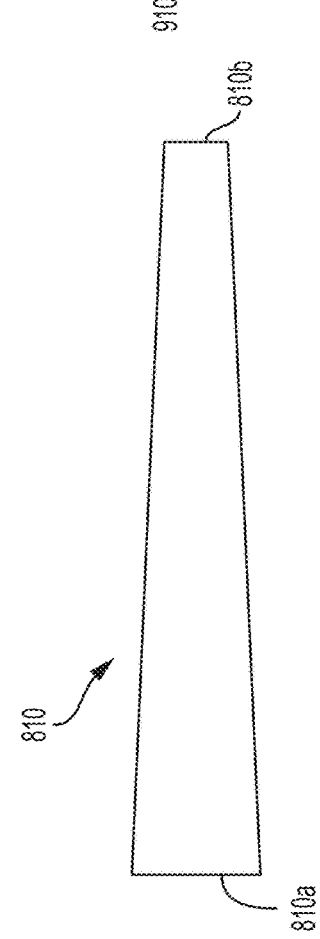
FIG. 7 is a side view of an exemplary embodiment of an ultrasonic blade having a tapered configuration.

The surgical devices generally include a housing having an instrument shaft extending therefrom and an end effector assembly having a clamping element and a ultrasonic blade. The instrument shaft includes a rotation assembly having an inner sleeve that is coupled to the clamping element of the end effector assembly. The inner sleeve is designed with a sliding mechanism. The sliding mechanism can have a variety of configurations. For example, as shown in FIGS. 1-2B, the sliding mechanism can have a slot-like configuration, or as shown in FIGS. 5-7, the sliding mechanism can have a channeled configuration.

Depending at least in part on the design of the end effector assembly, the surgical device can include one or more motors that actuate one or more assemblies of the instrument shaft as described in more detail below. In general, one or more motors can be used to drive various surgical device functions. The device functions can vary based on the particular type of end effector assembly, but in general a surgical device can include one or more motors that can be configured to cause a particular action or motion to occur, such as opening and/or closing of a clamping element such as a jaw, shaft and/or end effector assembly rotation, end effector assembly articulation, energy delivery to cut and/or coagulate tissue, etc. The motor(s) can be located within a housing of the surgical device or, in the alternative, coupled to the surgical device such as via a robotic surgical system. As described in more detail below, each motor can be configured to couple to or interact with one or more drive assemblies of the surgical device, e.g., a rotation drive assembly, an articulation drive assembly, a clamping drive assembly, and/or a shaft rotation drive assembly, so that the motor can actuate one or more elements to cause a variety of movements and actions of the device, e.g., to selectively rotate a clamping element relative to an ultrasonic blade, to selectively articulate the end effector assembly, to selectively move the clamping element towards and away from the ultrasonic blade, to selectively rotate the instrument shaft, etc. The motor(s) can be powered using various techniques, such as by a battery on or in the surgical device or by a power source connected through a robotic surgical system.

In certain embodiments, as discussed in more detail below, when the at least one motor is activated, it drives the rotation of at least one corresponding gear assembly located within a drive assembly of the surgical device, such as surgical devices 100 and 500 in FIGS. 1 and 5, respectively. The corresponding gear assembly can be coupled to at least one corresponding drive shaft, thereby causing linear and/or rotational movement of the at least corresponding drive shaft. While movement of two or more drive shafts can overlap during different stages of operation of the drive assemblies, each motor can be activated independently from each other such that movement of each corresponding drive shaft does not necessarily occur at the same time or during the same stage of operation.

Figure 2A:
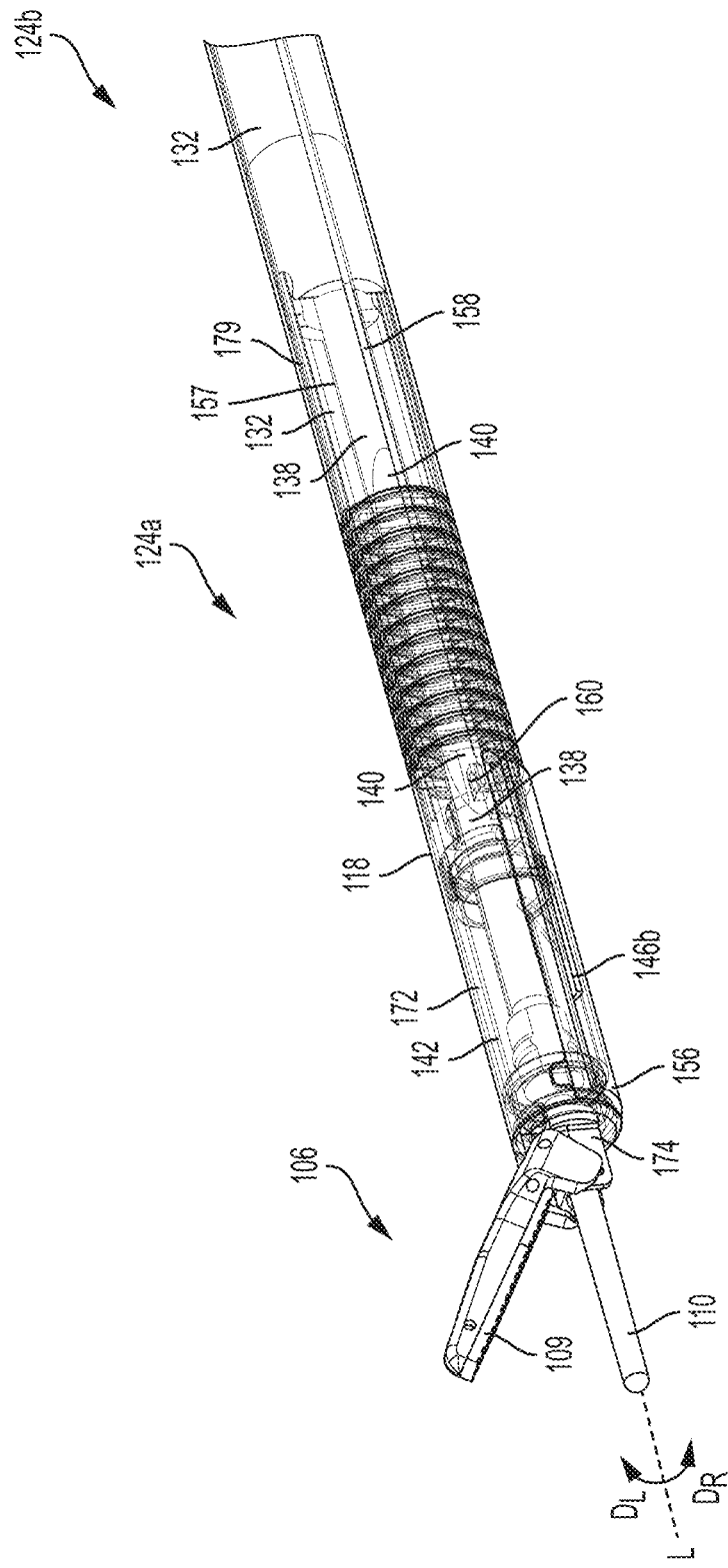
FIG. 2A is a perspective, partially transparent magnified view of a distal portion of the surgical device of FIG. 1.
Figure 2B:
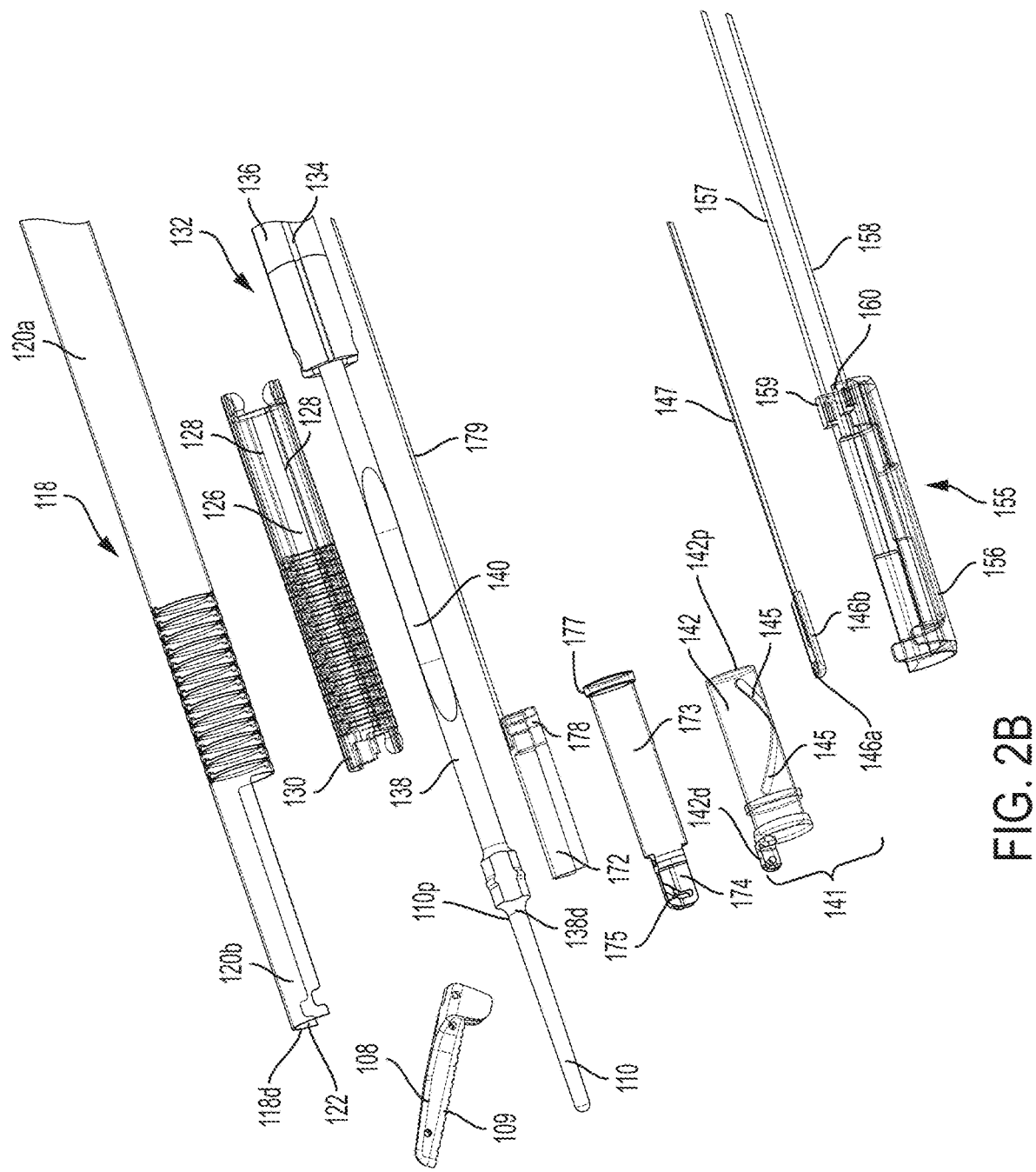
FIG. 2B is a partially exploded view of the distal portion of the surgical device of FIG. 2A.

FIGS. 1-3B illustrate an exemplary embodiment of a surgical device. As shown, the surgical device 100 includes a housing 102, an instrument shaft 104 extending from the housing 102, and an end effector assembly 106. The end effector assembly 106 includes a clamping element 108, such as a jaw, and an ultrasonic blade 110. In some implementations, as shown in FIGS. 1 and 2A-2B, the clamping element includes a clamp pad 109. As used herein, "housing" is used synonymously with "instrument housing." A person skilled in the art will appreciate that other ultrasonic end effector assemblies can be used with the surgical devices disclosed herein. Further, for purposes of simplicity only, certain components of the housing 102 are not illustrated in FIGS. 3A-3B.

Figure 3A:
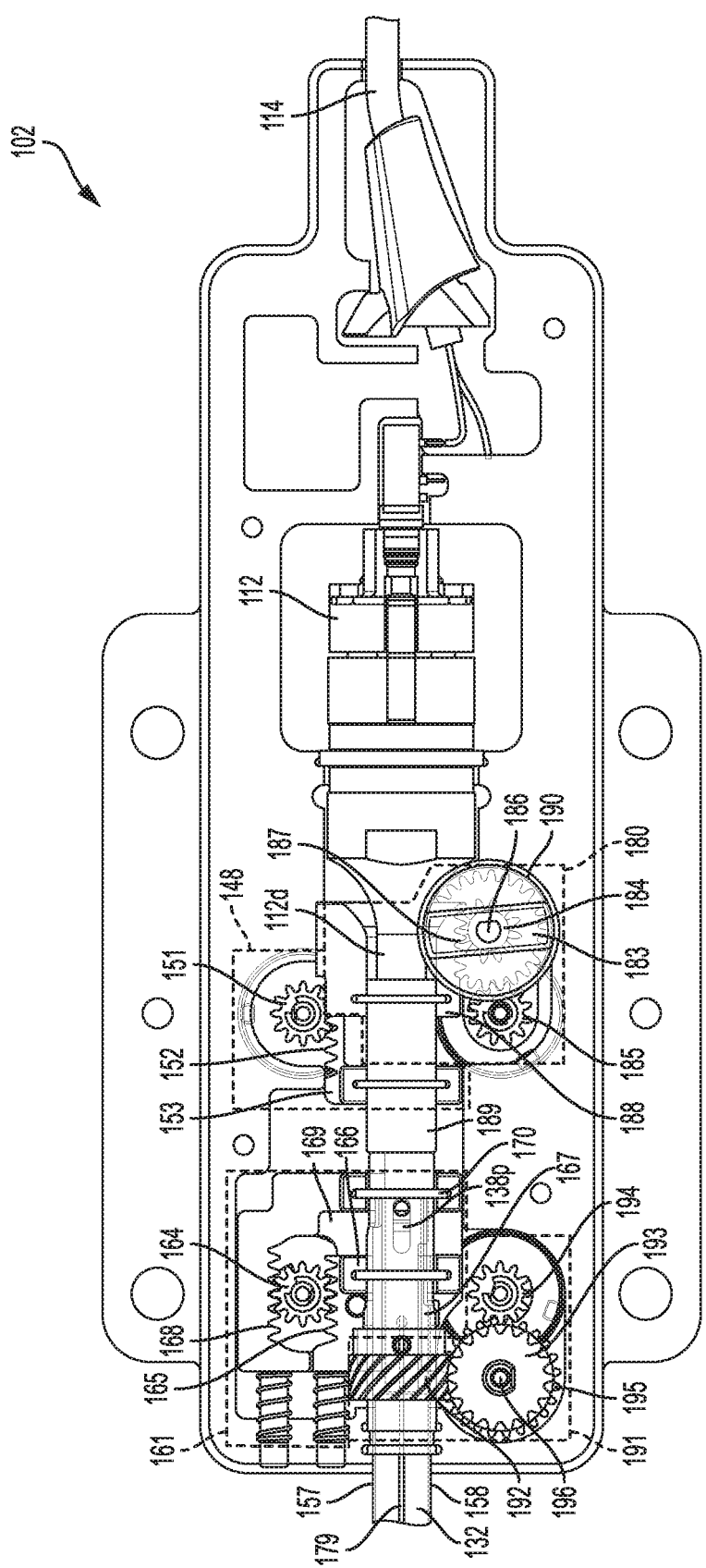
FIG. 3A is a top, partially transparent view of a proximal portion of the surgical device of FIG. 1.
Figure 3B:
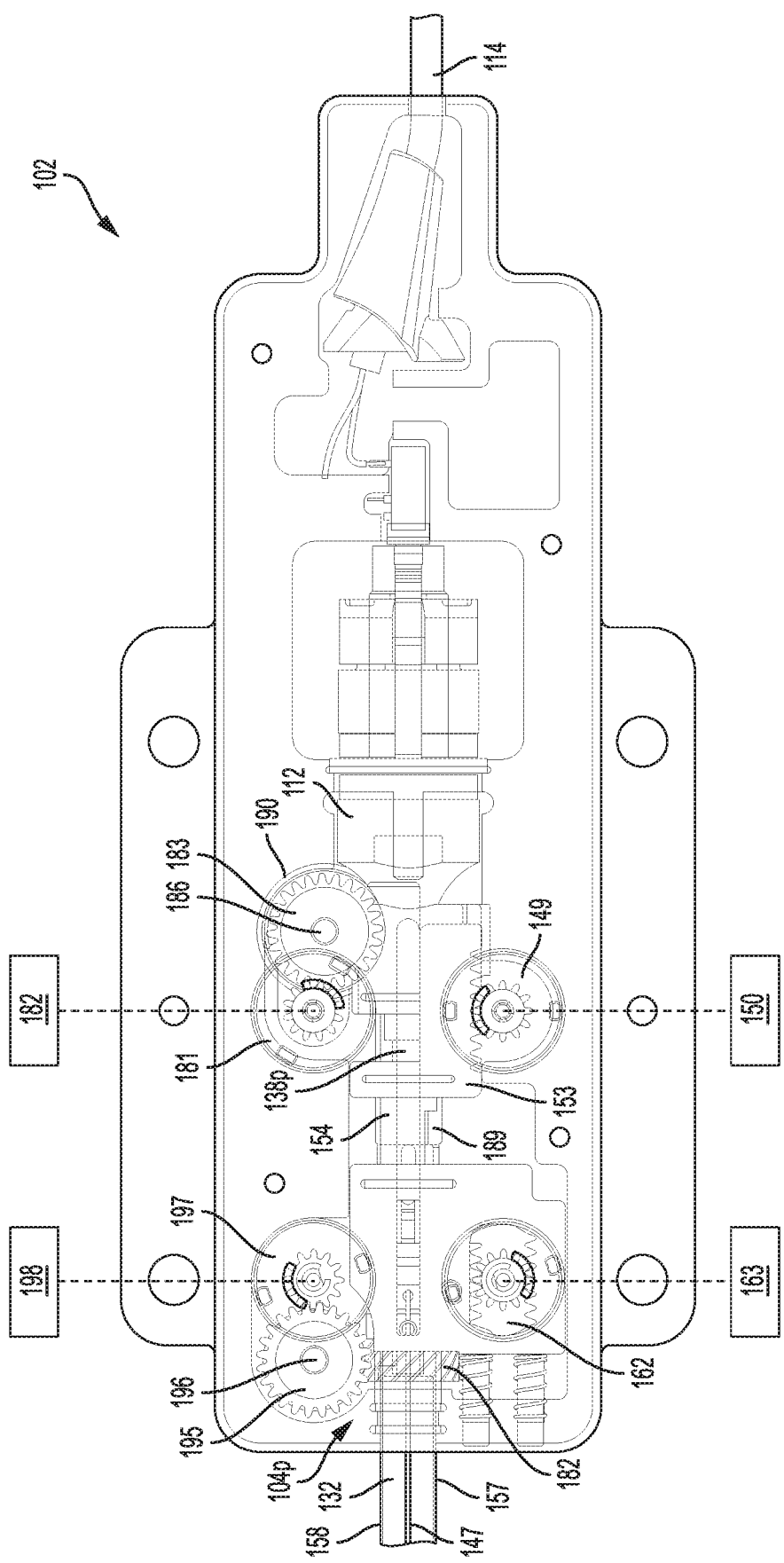
FIG. 3B is a bottom, partially transparent view of the proximal portion of the surgical device of FIG. 3A.
Figure 4:
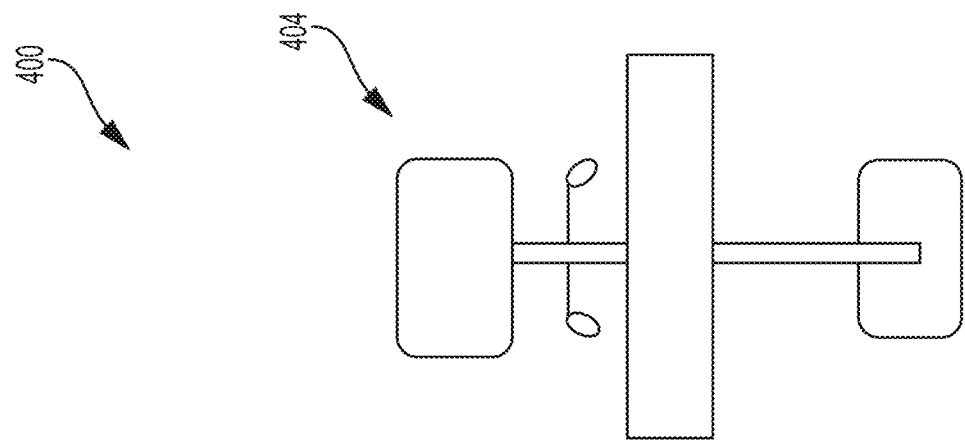
FIG. 4 is a perspective view of an exemplary embodiment of a surgical robotic system that includes a electromechanical arm having the surgical device of FIG. 1 mounted thereto, and being wirelessly coupled to a control system.
Figure 4:
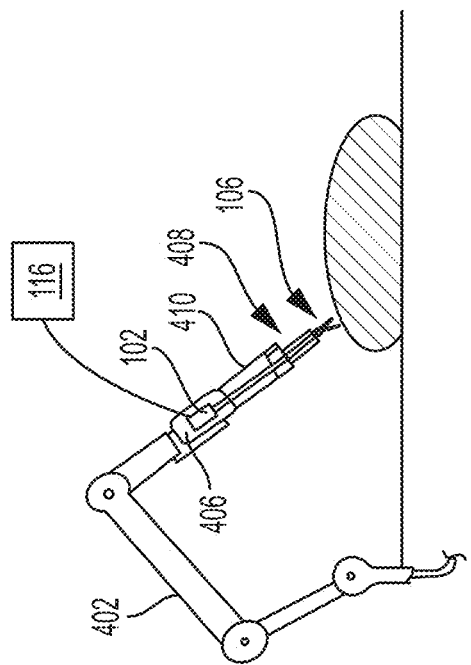

While the housing 102 can have a variety of configurations, in some implementations, as shown in FIGS. 1 and 3A-3B, the housing 102 is configured to be attached to a robotic system, such as robotic surgical system 400 shown in FIG. 4. Alternatively, the housing 102 can be designed for a hand-held device, for example as a handle housing. A person skilled in the art will appreciate that a housing designed for a hand-held device can require all or some of the elements disclosed herein and additional elements for operation. Details on exemplary housings for hand-held devices can be found, for example, in U.S. Pat. No. 9,095,367, which is incorporated by reference herein in its entirety. Further, the housing 102 can include various drive assemblies (e.g., four drive assemblies) that are configured to drive corresponding assemblies, such as rotation assembly 141, articulation assembly 155, clamping assembly, to effect motion and action of the surgical device, as discussed in more detail below.

As shown, the housing 102 includes an ultrasonic transducer 112. The ultrasonic transducer 112 is configured to convert electrical power into ultrasonic vibrations. While the ultrasonic transducer 112 can have a variety of configurations, in some implementations, as shown in FIGS. 1 and 3A-3B, the ultrasonic transducer 112 is mechanically engaged to at least one portion of the end effector assembly 106. As described in more detail below, in use, these ultrasonic vibrations are transmitted to at least a portion of the end effector assembly 106. The ultrasonic transducer 112 can receive electrical power from any suitable source. For example, in some instances, the ultrasonic transducer 112 can include a cable 114 that directly couples the ultrasonic transducer 112 with a generator 116. The generator 116 can include a power source and control module that can be configured to provide a power profile to ultrasonic transducer 112 that is suitable for the generation of ultrasonic vibrations through ultrasonic transducer 112. Optionally, the generator 116 can also be suitable for generation of RF energy.

In some embodiments, the generator 116 can include a GEN 300 sold by Ethicon Endo-Surgery, Inc. of Cincinnati, Ohio. Alternatively, or in addition to, the generator 116 can be constructed in accordance with the teachings of the following, alone or in combination: U.S. Pat. No. 8,986,302, entitled "Surgical Generator for Ultrasonic and Electrosurgical Devices"; and U.S. Pat. No. 9,095,367, "Flexible Harmonic Waveguides/Blades for Surgical Instruments, all of which are incorporated herein by reference in their entirety. Still other suitable forms that generator 116 can take, as well as various features and functionalities that generator 116 can provide, will be apparent to those skilled in the art in view of the teachings herein.

In some embodiments, at least part of the functionality of generator 116 can be incorporated directly into the housing 102. As an example, the housing 102 can include an integral battery or other integral power source, as well as any circuitry needed to condition power from a battery or other integral power source to drive ultrasonic transducer 112.

As discussed above, the instrument shaft 104 extends from the housing 102. While the instrument shaft 104 can have a variety of configurations, in some implementations, the instrument shaft 104, as shown in FIGS. 1-2B, includes an outer sleeve 118. While the outer sleeve 118 can have a variety of configurations, in some implementations, the outer sleeve 118, as shown, has a substantially tubular body 120a with a substantially semi-circular tip 120b at a distal portion thereof. As such, the distal end of the semi-circular tip 120b (e.g., a 180 degree shape) and the distal end 118d of the outer sleeve 118 are the same. It is also contemplated that the tip 120b can take the form of other suitable shapes and is not limited by the shape illustrated herein.

The outer sleeve 118 includes an articulable region 124a and a non-articulable region 124b. As shown, the articulable region 124a can have a ribbed or segmented configuration that can impart flexibility to the articulable region 124a such that the articulable region 124a can bend in various directions. Alternatively, or in addition, at least the articulable region 124a can be formed of a material that provides a desirable amount of flexibility to the outer sleeve 118. The non-articulable region 124b can define a longitudinal axis (L) of the device 100.

In certain embodiments, an articulation member 126 can be positioned within the outer sleeve 118 so as to substantially align with at least a portion of articulable region 124a of the outer sleeve 118. The articulation member 126 can be positioned between the tip 120b and the non-articulable region 124b of the outer sleeve 118, as shown in FIG. 2A. While the articulation member 126 can have a variety of configurations, in certain embodiments, as shown in FIGS. 2A-2B, the articulation member 126 can have a tubular configuration. Further, in some embodiments, the articulation member 126 can have a ribbed body configuration that is configured to align with a ribbed body configuration of the outer sleeve 118. The articulation member 126 can also include one or more elongated recess channels 128 that at least partially extend along the length of the articulation member 126. The one or more elongated recess channels 128 can be configured to allow for one or more actuator rods to extend through the instrument shaft 104 to effect various motions of the end effector assembly 106, as described in more detail below. Alternatively, or in addition, the articulation member 126 can have an outer diameter that provides suitable space between the inner surface 122 of the outer sleeve 118 and the outer surface 130 of the articulation member 126 so that the actuator rods can extend through this space, and consequently, through the instrument shaft 104.

In some embodiments, a rigid member 132 can be positioned within the outer sleeve 118 so as to substantially align with the non-articulable region 124b of outer sleeve 118. While the rigid member 132 can have a variety of configurations, in certain embodiments, as shown in FIGS. 1-2B, the rigid member 132 can have a tubular configuration. The rigid member 132 can also include one or more elongated recess channels 134 that at least partially extend along the length of the rigid member 132. The one or more elongated recess channels 134 can be configured to allow for one or more actuator rods to extend through the instrument shaft 104 to effect various motions of the end effector assembly 106, as discussed in more detail below. Alternatively, or in addition, the rigid member 132 can have an outer diameter that provides sufficient space between the inner surface 122 of the outer sleeve 118 and the outer surface 136 of the rigid member 132 so that the actuator rods can extend through this space, and consequently, the instrument shaft 104.

The instrument shaft 104 can also include a waveguide 138 that extends therethrough. As shown in FIGS. 1-2B, the waveguide 138 is in acoustic communication with the ultrasonic blade 110. The proximal end 110p of the ultrasonic blade 110 can be located at or near an antinode of the waveguide 138. For example, as shown, the distal end 138d of the waveguide 138 is acoustically coupled to the proximal end 110p of the ultrasonic blade 110. The ultrasonic blade 110 can be coupled to the waveguide 138 by any suitable means, for example, by an internal threaded connection, a welded joint, or the like. It is also contemplated that the waveguide 138 and the ultrasonic blade 110 can be formed as a single unitary piece. The proximal end 138p of the waveguide 138 can be received within the housing 102 such that it acoustically couples to the distal end 112d of the ultrasonic transducer 112. As such, the ultrasonic transducer 112, in use, converts received electrical power to ultrasonic vibrations that are transmitted along the waveguide 138 to the ultrasonic blade 110 to thereby facilitate cutting and/or sealing of tissue at the treatment site. The outer sleeve 118 of the instrument shaft 104 can isolate the outside environment (e.g., the patient or other surgical device(s) or equipment) from the ultrasonic vibrations of the waveguide 138.

While the waveguide 138 can have a variety of configurations, in some implementations, the waveguide 138, as shown in FIGS. 2A-2B, can include a flexible portion 140. As shown, the flexible portion 140 has a thinner cross-sectional area (e.g., a ribbon-like cross-sectional area shape) compared to the remaining portions of the waveguide. The flexible portion 140 can be aligned with a portion of the articulable region 124a of the outer sleeve 118 so that the end effector assembly 106 can deflect from a position aligned with a longitudinal axis (L) of the device 100, as discussed in more detail below. In this illustrated embodiment, the longitudinal axis (L) extends along the non-articulable region 124b of the outer sleeve 118. Additional details on suitable waveguides can be found in U.S. Pat. No. 9,095,367 and U.S. Patent Publication Nos. 2016/0296250 and 2016/0302819, which are each incorporated by reference herein in their entirety.

As discussed above, the instrument shaft 104 also includes a rotation assembly 141 that selectively effects rotation of the clamping element 108 relative to the ultrasonic blade 110. As such, in contrast to the shaft rotation drive assembly 191 as discussed in more detail below, the rotation assembly 141, and thus the rotation drive assembly 148, is configured to rotate the clamping element 108 while the ultrasonic blade 110 remains stationary. As shown in FIGS. 1 and 2A-2B, the rotation assembly 141 includes an inner sleeve 142 that is coupled to the clamping element 108. The structural configuration of the inner sleeve 142 is based at least in part on the structural configuration of other elements of the device 100, for example, the waveguide 138 the ultrasonic blade 110 itself, etc. As such, while the inner sleeve 142 can have a variety of configurations, in this illustrated embodiment, the inner sleeve 142 has a tubular configuration. The inner sleeve 142 can include a sliding mechanism, as described in detail below.

As shown, the sliding mechanism includes a slot 145. While the slot 145 can have a variety of configurations, in some implementations, as shown in FIGS. 2A-2B, the slot 145 can have a substantially spiral configuration about the inner sleeve 142. The slot 145 can extend entirely through the inner sleeve 142 as shown in FIGS. 2A-2B, or alternatively, the slot 145 can extend partially through the inner sleeve 142. The size and shape of the slot can vary. For example, as shown in FIGS. 2A-2B, the slot 145 extends along at least a portion of the inner sleeve 142. In one embodiment, the slot 145 can extend the entire length of the inner sleeve 142. A person skilled in the art will appreciate that the size and shape of the slot 145 is based at least in part on the size and shape of the inner sleeve 142.

The sliding mechanism also includes a pin 146a housed within the slot 145. The pin 146a extends from a pin plate 146b that is positioned between the inner sleeve 142 and the articulation pull 156. As discussed in more detail below, the pin 146a is configured to selectively slide within the slot 145 when a force is applied to an input operatively coupled to the pin 146a. Such sliding movement of the pin 146a within the slot 145 causes rotation of the inner sleeve 142 relative to the outer sleeve 118, and consequently, rotation the clamping element 108 relative to the ultrasonic blade 110.

For example, the pin plate 146b, and thus the pin 146a, is coupled to an actuator rod 147 that extends through the instrument shaft 104 and into the housing 102. While the actuator rod 147 can extend along any portion of the instrument shaft 104, the actuator rod 147, as shown in FIG. 3A, extends along a lower portion of the instrument shaft 104. This location may be desirable because it subjects the actuator rod 147 to a minimal length change when the end effector assembly 106 is articulated, thereby preventing the rotation of the clamping element 108 during articulation. In use, when the actuator rod 147 is actuated, the actuator rod 147 axially translates relative to the outer sleeve 118 to thereby cause rotation of the inner sleeve 142, and consequently the clamping element 108.

In use, when a force is applied to the actuator rod 147 (e.g., by an input operatively coupled thereto), the actuator rod 147 axially translates relative to the outer sleeve 118 to thereby cause the pin plate 146b to move causing the pin 146a to slide within the slot 145. As the pin 146a slides within the slot 145, the inner sleeve 142 is rotated and consequently the clamping element 108 relative to the ultrasonic blade 110. That is, when actuated, the actuator rod 147 moves in a first or a second direction causing the pin 146a to move in a corresponding direction. Depending on the directional movement of the actuator rod 147 the resulting rotation of the inner sleeve 142 and thus the clamping element 108, can rotate in a clockwise or counterclockwise direction. For example, in use, the actuator rod 147 can move in a distal direction causing the pin 146a to slide toward the distal end 142d of the inner sleeve 142. As a result, the inner sleeve 142 can rotate in a first direction (e.g., clockwise) thereby rotating the clamping element to a desirable position about the ultrasonic blade 110.

The amount of rotation of the inner sleeve 142 and thus the clamping element 108, will depend at least in part on the size and shape of the slot 145. In some embodiments, the inner sleeve 142 can rotate about 270 degrees about its center axis. In other embodiments, the inner sleeve 142 can rotate from about 180 degrees to about 270 degrees about its center axis. Further, the amount of rotation of the inner sleeve 142 can also depend on the amount of force being applied to the pin 146a.

The actuator rod 147 can be actuated in a variety of ways. For example, as shown in FIGS. 3A-3B, the rotation assembly 141 is operably coupled to a rotation drive assembly 148 that is configured to cause the actuator rod 147 to advance in distal and proximal directions relative to the outer sleeve 118. The rotation drive assembly 148, which is discussed in more detail below, can be located within the housing and coupled to a corresponding rotary driving disk 149, which is operatively coupled to a corresponding motor 150. During actuation, the motor 150 can actuate the rotation drive assembly 148. Exemplary motors for use with the systems and devices disclosed herein are described, for example, in U.S. Pat. Nos. 9,445,816 and 9,585,658 and in U.S. Patent Publication Nos. 2012/0292367 and 2015/0209059, each of which is incorporated by reference herein in its entirety. A person skilled in the art will appreciate that the elements of the rotation drive assembly 148 are not limited to what is shown in FIGS. 1 and 3A-3B, and thus other suitable rotation drive assemblies can include some or all of the features of the rotation drive assemblies described herein. Further, for purposes of simplicity, certain components of the rotation drive assembly 148 are not illustrated in FIGS. 3A-3B.

The rotation drive assembly 148 can have a variety of configurations. For example, as shown in FIGS. 3A-3B, the rotation drive assembly 148 can include a rotary drive gear 151 that is in meshing engagement with a gear rack 152 that is coupled to a translation block 153. The translation block 153 is connected to a drive shaft 154 extending therefrom. The actuator rod 147 is connected to the drive shaft 154 such that axial movement of the drive shaft 154 causes corresponding axial movement of the actuator rod 147. The rotary drive gear 151 can be operably coupled to the rotary driving disk 149 which is operatively coupled to the motor 150. In use, when the motor 150 is activated it drives rotation of the rotary driving disk 149. The rotation of the rotary driving disk 149 drives rotation of the rotary drive gear 151 causing substantially linear movement of the actuator rod 147 relative to the outer sleeve 118. It will be appreciated that the application of a rotary output motion from the motor 150 in one direction will result in substantially linear movement of the actuator rod 147 in a distal direction to slide the pin 146a towards a distal end 142d of the inner sleeve 142. Further, application of the rotary output motion in an opposite direction will result in substantially linear movement of the actuator rod 147 in a proximal direction to slide the pin 146a towards a proximal end 142p of the inner sleeve 142.

The instrument shaft 104 can also include additional assemblies to effect other motions or actions of the surgical device 100. For example, in some embodiments, the instrument shaft 104 can include an articulation assembly 155. Alternatively, or in addition to, the instrument shaft 104 can include a clamping assembly.

As shown in FIGS. 1 and 2A-2B, the instrument shaft 104 includes an articulation assembly 155 that is configured to deflect the end effector assembly 106 from a position aligned with a longitudinal axis (L) of the device 100. Further, in combination with the articulation assembly 155, the articulation of the end effector assembly 106 is accomplished through the articulable region 124a of the outer sleeve 118, the articulation member 126, and the flexible portion 140 of the waveguide 138. It is also contemplated herein that other suitable articulation assemblies can be used alone or in combination with one or more features of the surgical devices described herein. Non-limiting examples of other exemplary articulation assemblies can found in U.S. Patent Publication Nos. 2016/0296250, 2016/0296251, 2016/0296252, 2016/0296268, 2015/0320437, 2016/0374712, 2016/0302819, which are each incorporated by reference herein in their entirety.

While the articulation assembly 155 can have a variety of configurations, in some implementations, the articulation assembly 155, as shown in FIGS. 2A-2B, includes an articulation pull 156. The articulation pull 156 can have a variety of configurations. As shown, the articulation pull 156 has a substantially semi-circular configuration that complements the tip 120b of the outer sleeve 118 and is coupled thereto. It is also contemplated herein that the articulation pull 156 can take the form of other shapes. The illustrated articulation pull 156 is coupled to two actuator rods 157, 158 that each extend through the instrument shaft 104 and into the housing 102. As shown, the first actuator rod 157 is coupled to a first side end 159 of the articulation pull 156 and the second actuator rod 158 is coupled to a second opposing side end 160 of the articulation pull 156.

In use, when the end effector assembly 106 is aligned with the longitudinal axis of the device 100, actuation of the first and second actuator rods 157, 158 can cause the end effector assembly 106 to deflect from the longitudinal axis. For example, when the first actuator rod 157 is actuated, the first actuator rod 157 can distally advance relative to the housing 102, and when the second actuator rod 158 is actuated, the second actuator rod 158 can proximally retract relative to the housing 102 or vice versa. As a result, the axially translation of the first and second actuator rods 157, 158 facilitates articulation of the end effector assembly 106 at an angle relative to the longitudinal axis. It will be appreciated that the distal or proximal movement of the first and second actuator rods 157, 158 relative to the housing 102 drives the direction in which the end effector assembly 106 moves relative to the longitudinal axis (e.g., a left direction ($D_L$) or a right direction ($D_R$) as shown in FIG. 2A). Further, it will be appreciated that the movement of the end effector assembly relative 106 to the longitudinal axis depends at least in part on the movement of the flexible portion 140 of the waveguide 138 relative to the longitudinal axis. For example in some embodiments, the flexible portion 140 can articulate about 45 degrees or less relative to the longitudinal axis in one direction. In one other embodiments, the flexible portion 140 can articulate from about 35 degrees to 45 degrees relative to the longitudinal axis in one direction. In one embodiment, the flexible portion 140 can articulate from about 35 degrees to 40 degrees relative to the longitudinal axis in one direction.

The actuator rods 157, 158 can be actuated in a variety of ways. For example, as shown in FIGS. 1 and 3A-3B, the articulation assembly 155 is operably coupled to an articulation drive assembly 161 that is configured to cause each actuator rod 157, 158 to advance in distal and proximal directions relative to the housing 102. The articulation drive assembly 161, which is discussed in more detail below, can be located within the housing 102 and coupled to a corresponding rotary driving disk 149 which is operatively coupled to a corresponding motor 163. During actuation, the motor 163 can actuate the articulation drive assembly 161. Exemplary motors for use with the devices and systems disclosed herein are described, for example, in previously mentioned in U.S. Pat. Nos. 9,445,816 and 9,585,658 and in U.S. Patent Publication Nos. 2012/0292367 and 2015/0209059, each of which is incorporated by reference herein in its entirety. A person skilled in the art will appreciate that the elements of the articulation drive assembly 161 are not limited to what is shown in FIGS. 1 and 3A-3B, and thus other suitable articulation drive assemblies can include some or all of the features of the articulation drive assembly 161 described herein. Further, for purposes of simplicity, certain components of the articulation drive assembly 161 are not illustrated in FIGS. 3A-3B.

The articulation drive assembly 161 can have a variety of configurations. For example, as shown in FIGS. 3A-3B, the articulation drive assembly 161 can include a rotary drive gear 164 that is in meshing engagement with a first gear rack 165 that is coupled to a first translation block 166. The first translation block 166 is connected to a first drive shaft 167 extending therefrom. The first actuator rod 157 is connected to the first drive shaft 167 such that axial movement of the first drive shaft 167 causes corresponding axially movement of the first actuator rod 157. The rotary drive gear 164 is also in meshing engagement with a second gear rack 168 that is coupled to a second translation block 169. The second translation block 169 is connected to a second drive shaft 170 extending therefrom. The second actuator rod 158 is connected to the second drive shaft 170 such that axial movement of the second drive shaft 170 causes corresponding axially movement of the second actuator rod 158. As shown, the first and second gear racks 165, 168 oppose each other, such that the rotary drive gear 164 can concurrently engage the first and second gear racks 165, 168.

The rotary drive gear 164 can be operably coupled to the rotary driving disk 162 which is operatively coupled to the motor 163. In use, when the motor 163 is activated it drives rotation of the rotary driving disk 162. The rotation of the rotary driving disk 162 drives rotation of the rotary drive gear 164 causing substantially linear movement of the first actuator rod 157 relative to the housing 102 in a first direction (e.g., distal direction). The rotation of the rotary drive gear 164 also concurrently causes substantially linear movement of the second actuator rod 158 relative to the housing 102 in a second direction (e.g., proximal direction) that is opposite the first direction. It will be appreciated that the application of a rotary output motion from the motor 163 in one direction will result in substantially linear movement of the first actuator rod 157 in a distal direction and the second actuator rod 158 in a proximal direction so as to move the end effector assembly 106 in a first direction. Further, application of the rotary output motion in an opposite direction will result in substantially linear movement of the first actuator rod 157 in a proximal direction and the second actuator rod 158 in a distal direction so as to move the end effector assembly 106 in a second direction.

As discussed above, the instrument shaft 104 can include a clamping assembly. The clamping assembly can be configured to move the clamping element 108 relative to the instrument shaft 104 such that the clamping element 108 can selectively move towards and away from the ultrasonic blade 110. While the clamping assembly can have a variety of configurations, in some implementations, as shown in FIGS. 2A-2B, the clamping assembly includes a first pull member 172 and a second pull member 173, collectively referred to herein as a clamp pull. The clamp pull can be coupled to the clamping element 108 via a coupling element 174 located at the distal end of the second pull member 173. While the coupling element 174 can have a variety of configurations, in some implementations, the coupling element 174, as shown, includes two opposing channels 175 that are configured to receive complementary pins extending from an inner surface of the proximal end of the clamping element 108. The two opposing channels 175 can function as guides for the complementary pins to facilitate movement of the clamping element 108 towards and away from the ultrasonic blade 110.

The first and second pull members 172, 173 can have a variety of configurations. The first pull member 172, as shown, has a substantially semi-circular configuration and is positioned between the outer sleeve 118 and the inner sleeve 142. While the illustrated first pull member 172 is elongated, one skilled in the art will appreciate that the length of the first pull member 172 can vary. The second pull member 173, as shown, has a substantially tubular configuration and is positioned between the waveguide 138 and the inner sleeve 142. It is also contemplated herein that the first and second pull members 172, 173 can take the form of other shapes. Further, the first and second pull members 172, 173 are configured to engage or interact with each other such that axial translation of the first pull member 172, as discussed in detail below, effects corresponding axial translation of the second pull member 173, thereby moving the clamping element 108 towards or away from the ultrasonic blade 110. For example, as shown, a flange 177 is located at the proximal end of the second pull member 173. This flange 177 is configured to engage with a recessed channel 178 defined within first pull member 172. This engagement also allows the second pull member 173 to rotate with the inner sleeve 142 when the articulation assembly is actuated.

The illustrated clamp pull, in particular the first pull member 172, is coupled to an actuator rod 179 that extends through the instrument shaft 104 and into the housing 102. While the actuator rod 179 can extend along any portion of the instrument shaft 104, the actuator rod 179, as shown, can extend along an upper portion of the instrument shaft 104. This location may be desirable because it subjects the actuator rod 179 to a minimal length change when the end effector assembly 106 is articulated, thereby preventing the clamping element 108 to move toward the ultrasonic blade 110 during articulation. In use, when the actuator rod 179 is actuated, the actuator rod 179 axially translates relative to the outer sleeve 118 to thereby cause proximal or distal movement of the first pull member 172, and thus, the clamp pull.

In use, when the actuator rod 179 moves toward the housing 102 (e.g., from an initial position to a proximal position), the clamp pull and consequently the coupling element 174, retract toward the housing 102. This movement of the coupling element 174 causes the complementary pins of the clamping element 108 to slide within the two opposing channels 175 of the coupling element 174, and therefore facilitates movement of the clamping element 108 from its initial position (e.g., an open position) towards the ultrasonic blade 110 (e.g., a closed position). Once the clamping element 108 is in a closed position, a person skilled in the art will appreciate that moving the actuator rod 179 away from the housing 102 (e.g., in a distal direction) causes the clamp pull to also move in a similar direction. This movement causes the clamping element 108 to move away from the ultrasonic blade 110 thereby allowing clamping element 108 to move towards or return to its initial position. That is, moving the actuator rod 179 away from the housing 102 causes the complementary pins of the clamping element 108 to move towards or return to their initial position within the two opposing channels 175.

The actuator rod 179 can be advanced in a variety of ways. For example, as shown in FIGS. 1 and 3A-3B, the clamping assembly is operably coupled to a clamping drive assembly 180 that is configured to cause the actuator rod 179 to move in distal and proximal directions relative to the outer sleeve 118. The actuator clamping assembly, which is discussed in more detail below, can be disposed within the housing 102 and coupled to a corresponding rotary driving disk 181, which is operatively coupled to a corresponding motor 182. During actuation, the motor 182 can actuate the clamping drive assembly 180. Exemplary motors for use with the devices and systems disclosed herein are described, for example, in previously mentioned in U.S. Pat. Nos. 9,445,816 and 9,585,658 and in U.S. Patent Publication Nos. 2012/0292367 and 2015/0209059, each of which is incorporated by reference herein in its entirety. A person skilled in the art will appreciate that the elements of the clamping drive assembly 180 are not limited to what is shown in FIGS. 1 and 3A-3B, and thus other suitable clamping drive assemblies can include some or all of the features of the clamping drive assembly 180 described herein. Further, for purposes of simplicity, certain components of the clamping drive assembly 180 are not illustrated in FIGS. 3A-3B.

The clamping drive assembly 180 can have a variety of configurations. For example, as shown in FIGS. 3A-3B, the rotation drive assembly 148 can include three rotary gears 183, 184, 185. The first rotary gear 183 is operatively coupled to the second rotary gear 184 by a drive post 186. The first rotary gear 183 is also in meshing engagement with a gear rack 187 that is coupled to a translation block 188. The translation block 188 is connected to a drive shaft 189 extending therefrom. The actuator rod 179 is connected to the drive shaft 189 such that axial movement of the drive shaft 189 causes corresponding axially movement of the actuator rod 179. The second rotary gear 184 is in meshing engagement with the third rotary gear 185. The third rotary gear 185 can be operably coupled to the rotary driving disk 181 which is operatively coupled to the motor 182. In use, when the motor 182 is activated it drives rotation of the rotary driving disk 181. The rotation of the rotary driving disk 181 drives rotation of the third rotary gear 185, and consequently the first rotary gear 183, causing substantially linear movement of the actuator rod 179 relative to the housing 102. It will be appreciated that the application of a rotary output motion from the motor 182 in one direction will result in substantially linear movement of the actuator rod 179 in a proximal direction to move the clamp pull towards the housing 102. Further, application of the rotary output motion in an opposite direction will result in substantially linear movement of the actuator rod 179 in a distal direction to move the clamp pull away from the housing 102 and towards the distal end of the outer sleeve 118.

Alternatively, or in addition to, it may be desirable to manually advance or retract the actuator rod 179. For example, as shown in FIGS. 1 and 3A-3B, a rotation knob 190 can be operably coupled to the first rotary gear 183 via the drive post 186. In use, manual rotation of the rotation knob 190, and consequently the first rotary gear 183, would effect axial translation of the actuator rod 179 in a similar manner as described above.

In some embodiments, it may be desirable for the instrument shaft 104, and thus the entire end effector assembly, to rotate. As such, the rotation of the instrument shaft 104 can be effected by using a shaft rotation drive assembly. That is unlike the rotation assembly 141 and rotation drive assembly 148, a shaft rotation drive assembly as described herein effects rotation of an entire end effector assembly as opposed to only rotating the clamping element associated with an ultrasonic blade. For example, as shown in FIGS. 1 and 3A-3B, a shaft rotation drive assembly 191 is disposed within the housing 102. Further, for purposes of simplicity, certain components of the shaft rotation drive assembly 191 are not illustrated in FIGS. 3A-3B.

While the shaft rotation drive assembly 191 can have a variety of configurations, in some implementations, the shaft rotation drive assembly 191, as shown FIGS. 1 and 3A-3B, can include a first spiral worm gear 192 that is positioned at the proximal end 104p of the instrument shaft 104. The first spiral worm gear 192 is in meshing engagement with a second spiral worm gear 193 that is coupled to a first rotary drive gear 194 via a driving post 196. The first rotary drive gear 194 is in meshing engagement with a second rotary drive gear 195 that is operably coupled to a rotary driving disk 197 which is operatively coupled to a motor 198.

In use, the motor 198 rotates the rotary driving disk 197 which drives rotation of the second rotary drive gear 195, and consequently, the first spiral worm gear 192. This causes rotational movement of the instrument shaft 104 relative to the housing 102. It will be appreciated that the application of a rotary output motion from the motor 198 in one direction will result in substantially rotational movement of the instrument shaft 104 in a first direction (e.g., a clockwise direction). Further, application of the rotary output motion in an opposite direction will result in substantially rotational movement of the instrument shaft 104 in a second opposing direction (e.g., a counterclockwise direction).

Over the years a variety of minimally invasive robotic (or "telesurgical") systems have been developed to increase surgical dexterity as well as to permit a surgeon to operate on a patient in an intuitive manner. Many of such systems are disclosed in the following U.S. patents, which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,132,368, entitled "Multi-Component Telepresence System and Method", U.S. Pat. No. 6,231,565, entitled "Robotic Arm DLUS For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524,320, entitled "Mechanical Actuator Interface System For Robotic Surgical Tools", U.S. Pat. No. 7,691,098, entitled "Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Writed Monopolar Electrosurgical End Effectors". Many of such systems, however, have in the past been unable to generate the magnitude of forces required to effectively cut and fasten tissue. Many of such systems, however, have in the past been unable to facilitate articulation and rotation of an end effector assembly having a clamping element and an ultrasonic blade.

The surgical device 100 can be assembled in various ways. For example, to assembly the distal portion of the surgical device 100 illustrated in FIGS. 2A-2B can include the assembly of subunits which are then coupled together to form the resulting distal portion. In some embodiments, the assembly of a first subunit can include coupling the articulation member 126 to the rigid member 132 of the instrument shaft 104. The waveguide 138 and ultrasonic blade 110, which in this illustrated embodiment are a unitary structure, can then be slide through the rigid member 132 and the articulation member 126. After which each actuator rod 147, 157, 158, 179, where actuator rod 147 includes the pin 146a and pin plate 146b and actuator rod 179 includes the first pull member 172, can be placed into their respective recessed channels of the articulation member 126 and of the rigid member 132 thereby forming the first subunit. The first subunit is slide into the outer sleeve 118, such that the first pull member 172 and the pin 146a and pin plate 146b are located at the tip 120b of the outer sleeve 118. A second subunit can be formed by sliding the second pull member 173 and coupling element 174 through the inner sleeve 142. Thereafter the clamping element 108 can be attached to both the coupling element 174 and the inner sleeve 142 thereby coupling the second pull member 173 and inner sleeve 142 together. The second subunit can then be inserted into the instrument shaft 104, specifically at the tip 120b of the outer sleeve 118. The articulation pull 156 can be then placed over the second subunit and welded to the tip of the outer sleeve 118 to form the distal portion of the surgical device 100.

Accordingly, as discussed above, the surgical devices can be designed to be mounted to an electromechanical arm (e.g., a robotic arm). For example, FIG. 4 illustrates a robotic surgical system 400 having device 100 shown in FIGS. 1-3B mounted to an electromechanical arm 402. The electromechanical arm 402 can be wirelessly coupled to a control system 404 having a console with a display and two user input devices. One or more motors (not shown) are disposed within a motor housing 406 that is coupled to an end of the electromechanical arm 402. The housing 102 of surgical device 100 is mounted to the motor housing 406, and consequently to the electromechanical arm 402, to thereby operably couple the motor(s) to the various drive assemblies of surgical device 100. As a result, when the motor(s) are activated by the control system 404, the motor(s) can actuate one or more drive assemblies. As shown in FIG. 4, the instrument shaft 104 extends from the housing 102. During surgery, the instrument shaft 104 and end effector assembly 106, collectively the instrument shaft assembly for purposes of this description can be placed within and extend through a trocar 408 that is mounted on the bottom of a carrier 410 extending between the motor housing 406 and a trocar 408 support. The carrier 410 allows the instrument shaft assembly to be translated into and out of the trocar 408. Further, given that the end effector assembly 106 includes an ultrasonic blade 110, a generator 116 is operably coupled to the ultrasonic transducer 112 disposed within the housing 102. In use, when the generator 116 is activated, by the control system 404, the generator 116 delivers electrical energy to the ultrasonic transducer 112. The ultrasonic transducer 112 converts the electrical energy to ultrasonic vibrations that travel along the waveguide 138 to the ultrasonic blade 110 so that the ultrasonic blade 110 can cut and/or coagulate tissue at the treatment site. The electromechanical arm 402 is configured to support and move surgical device 100 as a whole along one or more degrees of freedom (e.g., all six Cartesian degrees of freedom, five or fewer Cartesian degrees of freedom, etc.).

Exemplary embodiments of motor operation and components of a housing or instrument housing (also referred to as a "puck") configured to be controlled by motors are further described in International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and in U.S. patent application Ser. No. 15/237,653 entitled "Methods, Systems, And Devices For Controlling A Motor Of A Robotic Surgical Systems" filed on Aug. 16, 2016, each of which is hereby incorporated by reference in its entirety.

Figure 5A:
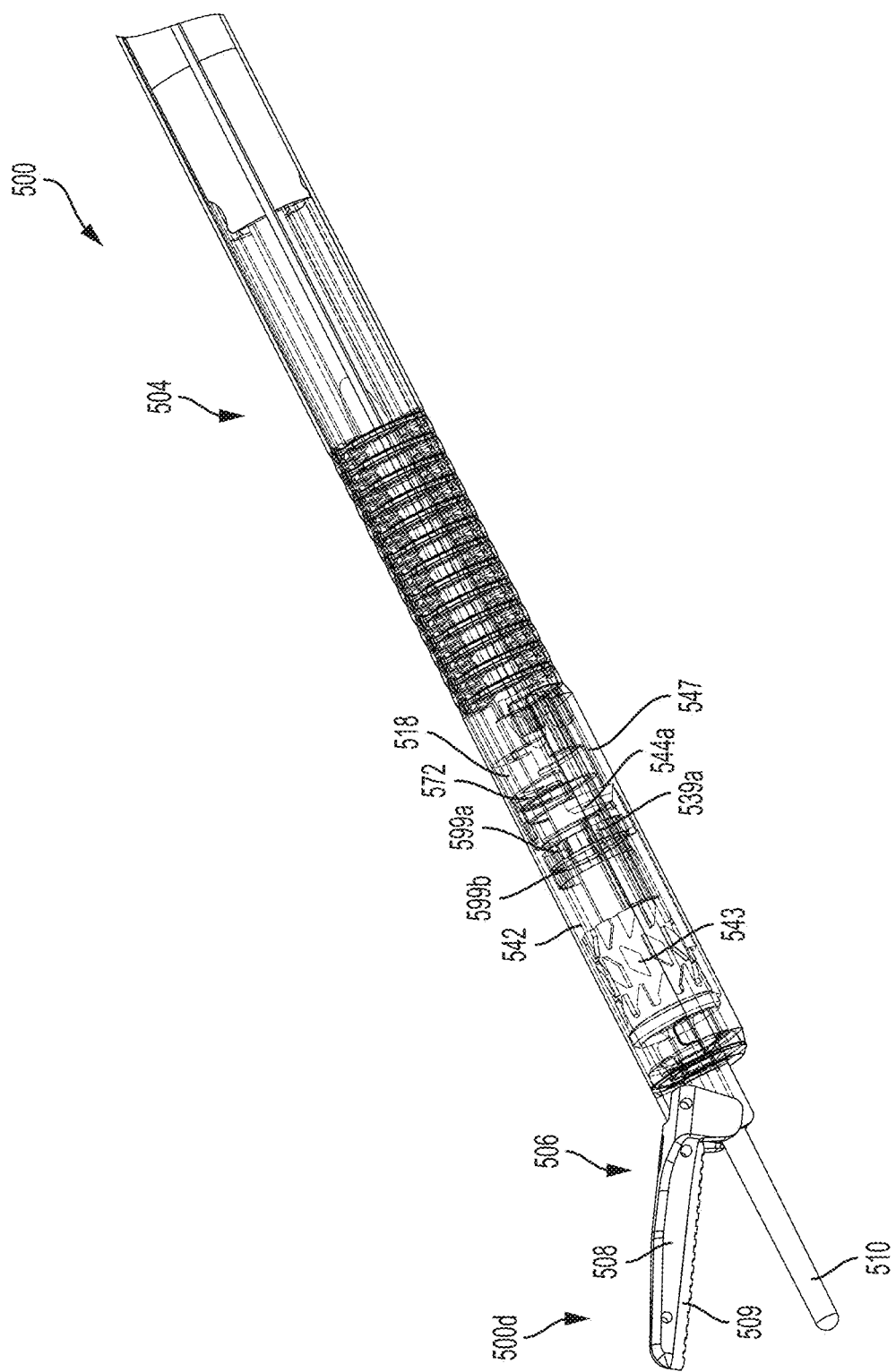
FIG. 5A is a perspective, partially transparent view of another exemplary embodiment of a distal portion of a surgical device having a rotation assembly having an inner sleeve.

FIGS. 5A-5B illustrate a distal portion of another exemplary embodiment of a surgical device 500 that includes a rotation assembly 541. Aside from the differences described in detail below, the surgical device 500 can be similar to surgical device 100 (FIGS. 1-3B) and is therefore not described in detail herein. As shown, the surgical device 500 includes an instrument shaft 504 that can extend from a housing, like housing 102 in FIG. 1. The instrument shaft 504 includes the rotation assembly 541 and a locking mechanism. The locking mechanism can include at least one locking assembly. As shown in FIGS. 5A-5B and described in more detail below, in this exemplary embodiment, the locking mechanism includes two locking assemblies.

As shown, the rotation assembly 541 includes an inner sleeve 542 that is coupled to a clamping element 508 having a clamping pad 509 coupled thereto. In this illustrated embodiment, the clamping element 508 is a jaw. The inner sleeve 542 extends from a first end 542d (e.g., a distal end) to a second end 542p (e.g., a proximal end) with an intermediate segment 542i extending therebetween. The inner sleeve 542 includes a sliding mechanism. While the sliding mechanism can have a variety of configurations, in some implementations, the sliding mechanism, as shown in FIGS. 5A-6, includes a predetermined pattern of projections 543 and one or more pins 546a (e.g., three pins), as discussed in more detail below.

As shown in FIGS. 5A-6, the predetermined pattern of projections 543 project radially outward from a portion of the intermediate segment 542i of the inner sleeve 542. The predetermined pattern of the projections 543 define channels 545 therebetween. While the predetermined pattern can have a variety of configurations, in some implementations, the predetermined pattern can include one or more rows of projections 543. For example, as shown in FIGS. 5A-6, the predetermined pattern includes three separate rows 543a, 543b, 543c of projections 543 that extend circumferentially around the inner sleeve 542. In some embodiments, one or more rows can be continuous, whereas in other embodiments, one or more rows can be discontinuous. In the illustrated embodiment, projections 543 of the first row 543a, which is the distal-most row on the inner sleeve 542, are interconnected to each other at their distal ends 543d. As a result, the first row 543a extends continuously around the inner sleeve 542 so as to help prevent the one or more pins 546a from sliding out of engagement with the channels 545 of the inner sleeve 542. The projections 543 of the second row 543b and of the third row 543c are discontinuous. It also contemplated herein that other predetermined patterns of projections 543 can be used with the surgical device 500.

The projections 543 within a single row can have the same shape and size. As shown, the projections 543 within the first row 543a have a first shape and size, the projections 543 in the second row 543b have a second shape and size, and the projections 543 in the third row 543c have a third shape. While the projections 543 within each row have the same shape and size, it is also contemplated herein that the projections 543 within a single row can have different shapes and sizes. Alternatively, the projections 543 of two or more rows can have the same or different shape and/or size. It will be appreciated that the shape and size of the projections 543 and the number of rows thereof depend at least in part on the size and shape of the inner sleeve 542, and therefore can vary accordingly.

The predetermined pattern of projections 543 is configured to define channels 545 therebetween so that the one of pins 546a can be selectively guided along the channels 545 in a predetermined path to rotate the inner sleeve 542 in a first direction or an opposing second direction. That is, as discussed in more detail below, the one or more pins 546a are configured to selectively slide within the channels 545 to cause rotation of the inner sleeve 542 relative to the outer sleeve 518, and consequently, rotation of the clamping element 508 relative to the ultrasonic blade 510 when a force is applied to an input operatively coupled to the one or more pins 546a.

For example, as shown in FIG. 5B, three pins 546a project radially inward from a distal end 546d of a pin plate 546b. While the pins 546a and the pin plate 546b can have a variety of configurations, in some implementations, as shown in FIG. 5B, the pins 546a each have a cylindrical shape and the pin plate 546b has an arcuate configuration. An actuator rod 547 is coupled a proximal portion 546p of the pin plate 546b, and thus the pins 546a. While the actuator rod 547 can extend along any portion of the instrument shaft 504, the actuator rod 547, as shown in FIG. 5A, can extend along a lower portion of the instrument shaft 504. This location may be desirable because it subjects the actuator rod 547 to a minimal length change when the end effector assembly 506 is articulated, thereby preventing the rotation of the clamping element 508 during articulation. When the actuator rod 547 is actuated, the actuator rod 547 axially translates relative to the outer sleeve 518 to thereby cause rotation of the inner sleeve 542, and consequently the clamping element 508.

In use, when a force is applied to the actuator rod 547 (e.g., by an input operatively coupled thereto), the actuator rod 547 axially translates relative to the outer sleeve 518 to thereby cause the pins 546a to slide within the channels 545 thereby rotating the inner sleeve 542, and consequently the clamping element 508 relative to the ultrasonic blade 510. That is, when actuated, the actuator rod 547 moves in a first or a second direction causing the pins 546a to move. Depending on the directional movement of the actuator rod 547, the rotation of the inner sleeve 542, and thus the clamping element 508, can rotate in a clockwise or counterclockwise direction. For example, in use, the actuator rod 547 can move in an initial distal direction causing the pins 546a to slide toward the first end 542d of the inner sleeve 542. As a result, the inner sleeve 542 can rotate in a first direction (e.g., clockwise) thereby rotating the clamping element 508 to a desirable position about the ultrasonic blade 510. It should be noted that the actuator rod 547 can subsequently move in a proximal direction that causes further rotation of the inner sleeve 542 in the first direction as described below.

Two exemplary guide paths for the one or more pins 546a to effect rotation of the inner sleeve 542 in a first direction D1 or a second direction D2 are illustrated in FIG. 6. For purposes of simplicity only, FIG. 6 illustrates the two exemplary guide paths for one pin 546a of the device 500 in FIGS. 5A-5B. However, since the three pins 546a are positioned equidistant from each other and from the distal end 546d of the pin plate 546b, the three pins 546a move concurrently in similar guide paths. In order to begin rotation of the inner sleeve 542 in a first direction D1 (e.g., a counterclockwise direction when viewing the device 500 from its proximal end, which is opposite its distal end 500d), the actuator rod 547 distally translates relative to the outer sleeve 518 thereby causing the pin 546a to distally advance from a first start position (PA) to a second position (P2) as shown in FIG. 6. A person skilled in the art will appreciate that the start position (PA) is exemplary and therefore the start position (PA) is not limited to the position illustrated in FIG. 6.

As the pin 546a begins to advance to the second position (P2), the pin plate 546b disengages a locking mechanism, as described in more detail below, so that the inner sleeve 542 can rotate. As the actuator rod 547 distally advances further, the pin 546a distally advances from the second position (P2) to a third position (P3) to begin rotation of the inner sleeve 542 in the first direction D1. To continue rotation of the inner sleeve 542 in the first direction D1, the actuator rod 547 retracts thereby causing the pin 546a to move from the third position (P3) to a fourth position (P4). As the actuator rod 547 retracts further, the pin 546a moves from the fourth position (P4) to a second start position (PB$_1$) to further rotate the inner sleeve 542 in the first direction D1 and ultimately reengage the locking mechanism, as discussed in detail below. This movement of the pin 546a (i.e., from PA to PB$_1$) can be repeated one or more times until the inner sleeve 542 has rotated a desirable amount in the first direction D1.

Alternatively, in order to begin rotation of the inner sleeve 542 in a second direction D2 (e.g., a clockwise direction when viewing the device 500 from its proximal end, which is opposite its distal end 500d), the actuator rod 547 proximally translates relative to the outer sleeve 518 thereby causing the pin 546a to retract from a first start position (PA) to a second position (P5), as shown in FIG. 6. A person skilled in the art will appreciate that the start position (PA) is exemplary and therefore the start position (PA) is not limited to the position illustrated in FIG. 6.

As the pin 546a begins to retract to a second position (P5), the pin plate 546b disengages a locking mechanism, as described in more detail below, so that the inner sleeve 542 can rotate. As the actuator rod 547 retracts further, the pin 546a retracts from the second position (P5) to a third position (P6) to begin rotation of the inner sleeve 542 in the second direction D2. To continue rotation of the inner sleeve 542 in the second direction D2, the actuator rod 547 distally advances thereby causing the pin 546a to move from the third position (P6) to a fourth position (P7). As the actuator rod 547 distally advances further, the pin 546a moves from the fourth position (P7) to a second start position (PB$_1$) so as to further rotate the inner sleeve 542 in the second direction D2 and ultimately reengage the locking mechanism, as discussed in detail below. This movement of the pin 546a (i.e., from PA to PB$_2$) can be repeated one or more times until the inner sleeve 542 has rotated a desirable amount in the second direction D2.

The amount of rotation of the inner sleeve 542, and thus the clamping element 508, will depend at least in part on the size of the pins 546a, the size of the inner sleeve 542, and the size and shape of the plurality of projections 543 and of the channels 545 defined therebetween. In some embodiments, the inner sleeve 542 can rotate about 360 degrees or less about its center axis. For example, in one embodiment, the inner sleeve 542 can rotate from about 1 degree to about 360 degrees about its center axis. In another embodiment, the inner sleeve 542 can rotate about 2 degrees to about 360 degrees about its center axis. In another embodiment, the inner sleeve 542 can rotate about 4 degrees to about 360 degrees about its center axis. Further, the amount of rotation of the inner sleeve 542 can also depend on the amount of force being applied to the pins 546a.

As shown in FIGS. 5A-6, the projections 543 of the first row 543a and the projections 543 of the third row 543c have substantially the same shape except that their respective ramp surfaces extend at opposing angles. That is, the ramp surfaces of the projections 543 in the first row 543a extend at a first angle ($\angle 1$), and the ramp surfaces of the projections 543 in the second row 543b extend at a second angle ($\angle 2$) that is opposite the first angle ($\angle 1$). As a result, the inner sleeve 542 can rotate 360 degrees in opposing directions continuously. To prevent this such that the inner sleeve 542 rotates in only one direction at one time, a locking mechanism can be within the instrument shaft 504 to promote unidirectional movement of the clamping element 508.

As mentioned above, initial movement of pin 546a disengages a locking mechanism to allow the inner sleeve 542 to rotate in a first direction or a second direction. While the locking mechanism can have a variety of configurations, in some implementations, the locking mechanism, as shown in FIGS. 5A-5B, includes two locking assemblies. The first locking assembly includes a first plurality of teeth 599a that extend circumferentially around a second end 542p of the inner sleeve 542 and a first spring arm 539a, configured to engage the first plurality of teeth 599a so as to prevent the inner sleeve 542 from rotating in the first direction D1 as shown in FIG. 6. The second locking assembly includes a second plurality of teeth 599b that extend circumferentially around a second end 542p of the inner sleeve 542 and a second spring arm 539b configured to engage the second plurality of teeth 599b so as to prevent the inner sleeve 542 from rotating in the second direction D2 as shown in FIG. 6. Thus, each locking assembly functions as a ratchet-like mechanism.

While the plurality of teeth can have a variety of configurations, in some implementations, as shown in FIGS. 5A-5B, the first and second plurality of teeth 599a, 599b have a ring-like configuration about the second end 542p of the inner sleeve 542.

As shown in FIG. 5B, the two spring arms 539a, 539b are coupled to and extending from opposing sides 559, 560 of the articulation pull 556. While the two spring arms 539a, 539b can have a variety of configurations, in some implementations, as shown in FIGS. 5A-5B, the two spring arms 539a, 539b each have an arcuate configuration. Further, the two spring arms 539a, 539b are offset from each other. This is because the first spring 539a is configured to engage the first plurality of teeth 599a so to prevent rotation of the inner sleeve 542 in the first direction D1 shown in FIG. 6, and the second spring arm 539b is configured to engage the second plurality of teeth 599b to prevent rotation of the inner sleeve 542 in the second direction D2, shown in FIG. 6. As such, when each spring arm 539a, 539b is engaged with their corresponding plurality of teeth 599a, 599b, the inner sleeve 542, and thus the clamping element 508, cannot rotate. As a result, as described in more detail below, when the inner sleeve 542 rotates in a first direction the first spring arm 539a is disengaged from the first plurality of teeth 599a while the second spring arm 539b remains engaged with the second plurality of teeth 599b. Likewise, when the inner sleeve 542 rotates in a second direction, the second spring arm 539b is disengaged from the second plurality of teeth 599b while the first spring arm 539a remains engaged with the first plurality of teeth 599a.

To disengage and reengage a locking assembly, the pin plate 546b includes two unlock arms 544a, 544b that extend from opposing sides of the pin plate 546b. While the two unlock arms 544a, 544b can have a variety of configurations, in some implementations, as shown in FIGS. 5A-5B, the two unlock arms 544a, 544b each have an arcuate configuration. Further, the two unlock arms 544a, 544b are offset from each other. This is because the first unlock arm 544a is configured to disengage the first spring arm 539a from the first plurality of teeth 599a to allow the inner sleeve 542 to rotate in the first direction D1 shown in FIG. 6. Likewise, the second unlock arm 544b is configured to disengage the second spring arm 539b from the second plurality of teeth 599b to allow the inner sleeve 542 to rotate in the second direction D1 shown in FIG. 6. As such, the first unlock arm 544a and the second unlock arm 544b can be configured to interact with the first spring arm 539a and the second spring arm 539b, respectively, so as to disengage one of the locking assemblies to allow the inner sleeve 542 to rotate in a first or a second direction.

In use, as described above, as the pin 546a begins to distally advance to the second position (P2), the pin plate 546b disengages the first locking assembly by moving the first spring arm 539a. That is, as the actuator rod 547 begins to distally advance, and thus the pin 546a to distally move from its starting position (PA), the first unlock arm 544a of the pin plate 546b also distally moves. As a result, the distal movement of the first unlock arm 544a causes the first spring arm 539a to distally move, and consequently disengage from the first plurality of teeth 599a. This disengagement allows the inner sleeve 542 to move in the first direction D1 as shown in FIG. 6. The first locking assembly is disengaged until the pin 546a moves into the second starting position ($PB_1$).

As described above, to move the inner sleeve 542 in the second direction D2 as shown in FIG. 6, the pin 546a begins to retract from it starting position (PA) to a second position (P5), causing the pin plate 546b to disengage the second locking assembly by moving the second spring arm 539b. That is, as the actuator rod 547 begins to proximally translate, and thus the pin 546a from its starting position (PA), the second unlock arm 544b of the pin plate 546b also retracts. As a result, the proximal movement of the second unlock arm 544b causes the second spring arm 539b to proximally move. The proximal movement of the second spring arm 539b causes it to disengage from the second plurality of teeth 599b to allow the inner sleeve 542 to move in the second direction D2 as shown in FIG. 6. The second locking assembly is disengaged until the pin 546a moves into the second starting position ($PB_2$).

Alternatively, the locking mechanism can include a friction spring arm that is configured to apply to a predetermined frictional force to the inner sleeve 542 so as to prevent the inner sleeve 542 from rotating until a driving force applied to a rotation assembly, like rotation assembly 141 in FIGS. 3A and 3B exceeds the predetermined frictional force. Further, the friction spring arm can be configured to allow unidirectional rotation of the inner sleeve, and therefore allow the inner sleeve to move in a first direction or a second direction opposite the first direction. The inner surface of the friction spring arm can include surface features, for example bumps extending from the inner surface, to create or enhance the predetermined frictional force to the inner sleeve 542. Alternatively, or in addition, the inner sleeve 542 can include surfaces features that align with the inner surface of the friction spring arm to create or enhance the predetermined frictional force.

Further, the clamping assembly of surgical device 500 in FIGS. 5A-5B is similar to the clamping assembly of surgical device 100 in FIGS. 1-2A except for the length of the first pull member 572. That is, the first pull member 572 of surgical device 500 in FIGS. 5A-5B is shorter in length compared to the length of first pull member 172 of surgical device 100 in FIGS. 1-2B. Aside from this structural difference, the clamping assembly of surgical device 500 functions similarly to clamping assembly of surgical device 100 in FIGS. 1-2A.

As discussed above, an end effector assembly, like end effector assembly 106 and 506 in FIGS. 1-3B and 5A-5B, respectively, can include an ultrasonic blade, like ultrasonic blade 110 and 510 in FIGS. 1-3B and 5A-5B, respectively. As such, the ultrasonic blade can extend from a first end (e.g., a proximal end) to a second end (e.g., a distal end) in which the first end can be in acoustic communication with a waveguide, like waveguide 138 in FIGS. 1-2B. In some embodiments, the ultrasonic blade can be axisymmetric. By having using an axisymmetric ultrasonic blade, the closure geometry of the end effector assembly can be the same for any position of the clamping element.

The ultrasonic blade can have a variety of configurations. For example, as shown in FIGS. 1-2B and 5A-5B, an ultrasonic blade can have a substantially straight (e.g., non-tapered) configuration, as shown in FIGS. 1-3B and 5-6B. Alternatively, as shown in FIG. 7, an ultrasonic blade 810 can have a tapered configuration (e.g., a conical taper from the first end 810a to the second end 810b of the ultrasonic blade 810). A tapered configuration can beneficially provide additional space for rotating the clamping element about the ultrasonic blade.

Figure 8:
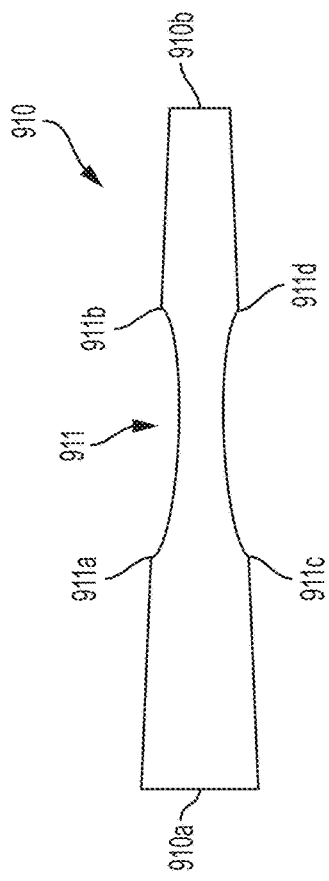
FIG. 8 is a side view of an exemplary embodiment of an ultrasonic blade having tapered configuration with a concave shaped portion.

Similarly, as shown in FIG. 8, the ultrasonic blade 910 can have a tapered configuration with a concave shaped portion 911 positioned between the first and second ends 910a, 910b of the ultrasonic blade 910. The concave shaped portion 911 can substantially prevent slidable movement of tissue that is captured between a clamping element and the ultrasonic blade 910. That is, the concave portion can allow for cradling of clamped tissue to aid in the dissection thereof. The interface of the concave shaped portion 911 with the remaining portions of the ultrasonic blade 910 can define one or more edges 911a, 911b, 911c, 911d. In some instances, the edges can be rounded. The concave shaped portion 911 can be positioned at various distances from the first and second ends 910a, 910b. In some embodiments, the concave shaped portion 911 can be positioned equidistantly from the first and second ends 910a, 910b of the ultrasonic blade 910. Further, in some embodiments, a clamping element that can be used with the ultrasonic blade 910 to treat tissue can include a clamp pad having a convex shaped portion complementary to the concave shaped portion 911 of the ultrasonic blade 910.

Further, the ultrasonic blade can have a variety of cross-sectional shapes. For example, the ultrasonic blade, like ultrasonic blade 110 and 510, shown in FIGS. 1-2B and 5A-5B, respectively, can have a substantially circular cross-sectional shape. Alternatively, the ultrasonic blade can have two or more blade surfaces arranged around the longitudinal axis of the ultrasonic blade in which the two or blade surfaces define a blade cross-sectional shape profile.

Figure 9:
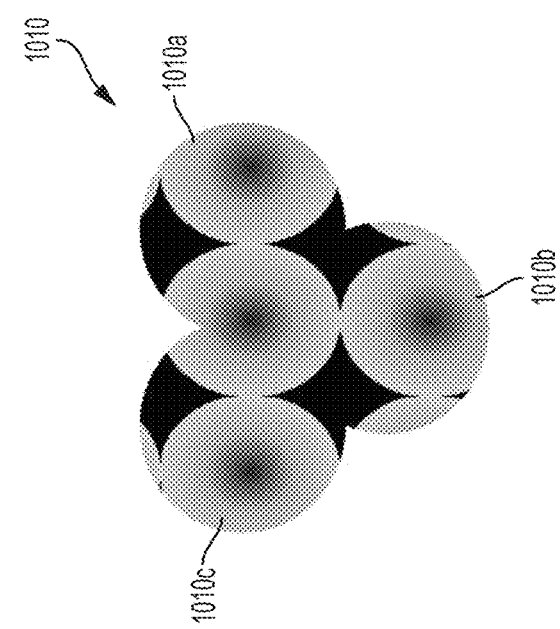
FIG. 9 is a front cross-sectional view of an exemplary embodiment of an ultrasonic blade having overlapping subunits, where each subunit has a substantially circular cross-sectional shape.

For example, in some embodiments, the ultrasonic blade can have two or more subunits that partially overlap with one another to create an overall cross-sectional shape having a local pressure profile that promotes sealing of tissue that is captured between a clamping element and the ultrasonic blade. Each subunit can have a predetermined cross-sectional shape (e.g., a geometric shape) and surface area in which the summation of the surface area of each subunit is greater than a surface area of the ultrasonic blade. As shown in FIG. 9, the ultrasonic blade 1010 includes three subunits 1010a, 1010b, 1010c, where each subunit 1010a, 1010b, 1010c has a substantially circular cross-sectional shape. The radii of each subunit 1010a, 1010b, 1010c can be sized so as to provide a local pressure profile that can enhance effective sealing of tissue. Further, while not necessary, the subunit units 1010a, 1010b, 1010c as shown in FIG. 9 are uniformly placed about the ultrasonic blade with respect to angle relative to the longitudinal axis of the ultrasonic blade.

Figure 10:
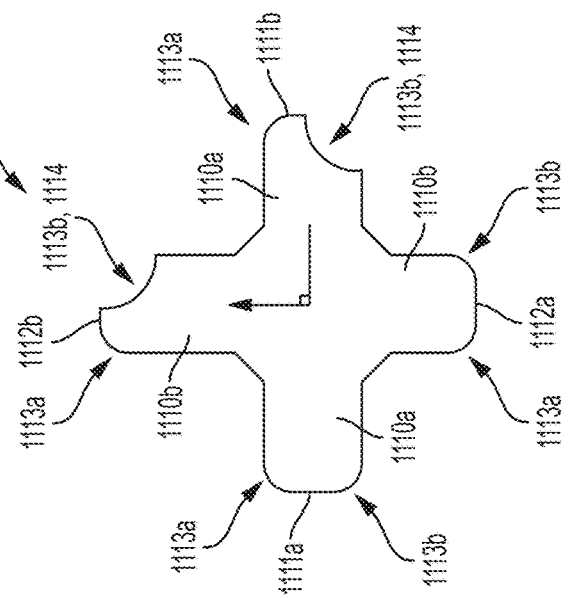
FIG. 10 is a front cross-sectional view of an exemplary embodiment of an ultrasonic blade having a cross-like configuration.

In other embodiments, the ultrasonic blade can have two or more intersecting blades. For example, in one embodiment, as shown in FIG. 10, the ultrasonic blade 1110 can include a first blade 1110a and a second blade 1110b that intersect at the central axis of the ultrasonic blade to form a cross-like cross-sectional shape. The central axis extends longitudinally between the first and second ends of the ultrasonic blade. The first and second blades, collectively the ultrasonic blade, can intersect each other at a variety angles. For example, as illustrated in FIG. 10, the ultrasonic blade 1110 includes a first blade 1110a and a second blade 1110b that intersect each other at an angle of about 90 degrees relative to each other. It is also contemplated herein that the first and second blades 1110a, 1110b can intersect each other at an angle other than 90 degrees relative to each other. A person skilled in the art will appreciate that the intersect angle of two or more blades depend at least in part on the number of blades and the outer diameter of each blade.

Each blade 1110a, 1110b can have at least one tissue-contacting surfaces that is configured for sealing clamped tissue. Each blade 1110a, 1110b can also have at least one tissue-contacting surface that is configured for back-cutting unclamped tissue. As shown in FIG. 10, each blade 1110a, 1110b extends a length from a first end 1111a, 1111b to a second end 1112a, 1112b. A person skilled in the art will appreciate that the length of each blade 1110a, 1110b can be varied, for example, to minimize inadvertent contact with other surfaces. Further, the lengths can change with axial positions to thereby effect the same tissue contacting surfaces as in a tapered blade. Each end 1111a, 1111b, 1112a, 1112b can extend between two edges 1113a, 1113b. As shown, at least one edge is a fillet edge 1114. The fillet edge 1114 can be configured for back-cutting of unclamped tissue. As shown, the remaining edges are rounded. It will be appreciated that the geometry of the edges can be varied. For example, in one embodiment, all of the edges can be rounded. While the ultrasonic blade 1110 is not balanced with equal chamfers, it is contemplated herein that the edge features may vary, e.g., vary in size or geometry, to balance the ultrasonic blade.

As previously mentioned, the surgical devices and systems can be used treat tissue. Any suitable method can be used for operating any surgical devices and systems described herein. For example, when operating the surgical device 100 (FIGS. 1-3B), the device 100 can be directed to a surgical site. Prior to, during, or after directing the surgical device 100 to the surgical site, the clamping element 108 can be selectively rotated relative to the ultrasonic blade 110. In certain instances, the clamping element 108 can rotated in the range of about 1 degrees to about 360 degrees. Once tissue is disposed between the clamping element 108 and the ultrasonic blade 110, the clamping assembly can be selectively actuated to cause the clamping element 108 to move toward the ultrasonic blade 110, which in turn, applies a clamping force to the tissue. It will be appreciated that rotation of the clamping element 108 is not necessary for the clamping assembly to be actuated. Once tissue is clamped between the clamping element 108 and the ultrasonic blade 110, ultrasonic energy can be transmitted to the ultrasonic blade 110 (e.g., by the ultrasonic transducer 112) to treat the clamped tissue. In certain instances, the instrument shaft 104 is attached to a robotic surgical system, like robotic surgical system 400 shown in FIG. 4.

In some embodiments, the instrument shaft 104 can be selectively articulated such that the end effector assembly 106 is angularly oriented with respect to a longitudinal axis of a proximal portion of the instrument shaft 104. As such, the clamping element 108 can rotate when the clamping element 108 is in an articulated condition.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A surgical device, comprising:
   a housing;
   an instrument shaft extending from the housing, the instrument shaft including an outer sleeve having an articulable region and a non-articulable region, the instrument shaft further including,
      a waveguide that is acoustically coupled to an ultrasonic transducer, wherein a portion of the articulable region is aligned with a flexible portion of the waveguide, and
      a rotation assembly having an inner sleeve; and
   an end effector assembly at a distal end of the outer sleeve, the end effector assembly having a clamping element and an ultrasonic blade that is in acoustic communication with the waveguide,
   wherein the inner sleeve is coupled to the clamping element, the inner sleeve having a sliding mechanism that is configured to selectively rotate the clamping element relative to the ultrasonic blade, the sliding mechanism having a predetermined pattern of projections that project radially outward from the inner sleeve to form channels therebetween and one or more pins that are configured to selectively slide within the channels upon a force applied to an input operatively coupled to the one or more pins to thereby cause rotation of the clamping element.

2. The device of claim 1, wherein the instrument shaft includes two spring arms that are each configured to engage a plurality of teeth that extend circumferentially around a proximal end of the inner sleeve, and wherein the first spring arm is configured to engage a first plurality of teeth to prevent rotation of the inner sleeve relative to the outer sleeve in a first direction and the second spring arm is configured to engage a second plurality of teeth to prevent rotation of the inner sleeve relative to the outer sleeve in a second direction.

3. The device of claim 1, wherein the instrument shaft includes a clamping assembly coupled to the end effector assembly, the clamping assembly being configured to drive movement of the clamping element relative to the instrument shaft such that the clamping element selectively moves towards and away from the ultrasonic blade.

4. The device of claim 3, wherein the clamping assembly comprises a clamp pull that is coupled to the clamping element, the clamp pull being configured to axially translate relative to the outer sleeve to cause the clamping element to move towards and away from the ultrasonic blade.

5. The device of claim 1, further comprising an articulation assembly that is configured to selectively deflect the end effector assembly from a position aligned with a longitudinal axis, wherein the longitudinal axis extends along the non-articulable region of the outer sleeve.

6. The device of claim 1, wherein the housing is attached to a robotic surgical system.

7. A robotic surgical system, comprising:
   an electromechanical arm having a motor disposed therein;
   an instrument housing mounted to the electromechanical arm;
   an instrument shaft extending from the housing, the instrument shaft including an outer sleeve and further including,
      an articulable ultrasonic waveguide acoustically coupled to an ultrasonic transducer and extending through the instrument shaft,
      an actuation assembly having a first actuator rod that is operably coupled to the motor, and
      a rotation assembly having an inner sleeve that includes a predetermined pattern of projections that project radially outward from the inner sleeve to form channels therebetween and one or more pins coupled to a distal end of the first actuator rod; and
   an end effector assembly formed at a distal end of the outer sleeve, the end effector assembly having a jaw and an ultrasonic blade that is acoustically coupled to the articulable ultrasonic waveguide, wherein the actuation assembly is operatively coupled to the jaw, and wherein the first actuator rod is configured to axially translate relative to the outer sleeve to slide the one or more pins within the channels to selectively rotate the jaw while the ultrasonic blade remains stationary.

8. The system of claim 7, wherein the actuation assembly includes a second actuator rod that is operable coupled to the motor, and wherein the second actuator rod is configured to axially translate relative to the outer sleeve to selectively move the jaw towards and away from the ultrasonic blade.

9. The system of claim 7, wherein the instrument shaft includes a locking mechanism that is configured to selectively promote unidirectional rotation of the jaw.

10. The system of claim 7, wherein the instrument shaft includes a clamping assembly having a jaw pull that is configured to axially translate relative to the outer sleeve to thereby cause the jaw to open and close so as to clamp tissue between the jaw and the ultrasonic blade.

11. The system of claim 7, further comprising an articulation assembly that is configured to deflect the end effector assembly from a position aligned with a longitudinal axis, wherein the longitudinal axis extends along a non-articulable section of the outer sleeve.

12. The system of claim 7, wherein the instrument shaft includes two spring arms that are each configured to engage a plurality of teeth that extend circumferentially around a proximal end of the inner sleeve, and wherein the first spring arm is configured to engage a first plurality of teeth to prevent rotation of the inner sleeve relative to the outer sleeve in a first direction and the second spring arm is configured to engage a second plurality of projections to prevent rotation of the inner sleeve relative to the outer sleeve in a second direction.

13. A method, comprising:
  directing a surgical device having an end effector assembly to a surgical site, the end effector assembly operably coupled to an instrument shaft that contains an ultrasonic waveguide and a rotation assembly, the end effector assembly having an ultrasonic blade and a clamping element, the rotation assembly having an inner sleeve that is operatively coupled to the clamping element and includes a predetermined pattern of projections that project radially outward from the inner sleeve to form channels therebetween and one or more pins;
  selectively rotating the clamping element relative to the ultrasonic blade;
  selectively actuating a clamping assembly to cause the clamping element to move towards the ultrasonic blade to and thereby apply a clamping force to tissue disposed between the clamping element and the ultrasonic blade; and
  transmitting ultrasonic energy to the ultrasonic blade to treat the tissue clamped between the clamping element and the ultrasonic blade.

14. The method of claim 13, further comprising selectively articulating the instrument shaft such that the end effector assembly is angularly oriented with respect to a longitudinal axis of a proximal portion of the instrument shaft extending from a housing.

15. The method of claim 14, wherein the clamping element is able to rotate when the clamping element is in an articulated condition.

16. The method of claim 13, wherein the clamping element is able to rotate in the range of about 1 degree to about 360 degrees.

17. The method of claim 13, wherein the instrument shaft is attached to a robotic surgical system.

18. The method of claim 13, wherein selectively rotating the clamping element comprises sliding the one or more pins within the channels of the inner sleeve to cause the inner sleeve to rotate and thereby rotate the clamping element.

19. The method of claim 18, wherein the instrument shaft includes an outer sleeve and an actuator rod operably coupled to the one or more pins, and wherein selectively rotating the clamping element comprises axially translating the actuator rod relative to the outer sleeve to cause the one or more pins to slide within the channels of the inner sleeve to rotate the inner sleeve.

* * * * *